US012097203B2

(12) United States Patent
Shojaei et al.

(10) Patent No.: US 12,097,203 B2
(45) Date of Patent: Sep. 24, 2024

(54) COMBINATION THERAPIES COMPRISING SHP2 INHIBITORS AND PD-1 INHIBITORS

(71) Applicant: HUYABIO International, LLC, San Diego, CA (US)

(72) Inventors: Farbod Shojaei, San Diego, CA (US); Jill M. Ricono, San Diego, CA (US); Robert Goodenow, San Diego, CA (US); Mireille Gillings, San Diego, CA (US)

(73) Assignee: HUYABIO International, LLC, San Diego, CA (US)

( * ) Notice: Subject to any disclaimer, the term of this patent is extended or adjusted under 35 U.S.C. 154(b) by 0 days.

(21) Appl. No.: 17/736,879

(22) Filed: May 4, 2022

(65) Prior Publication Data

US 2022/0370457 A1    Nov. 24, 2022

Related U.S. Application Data

(60) Provisional application No. 63/320,997, filed on Mar. 17, 2022, provisional application No. 63/184,685, filed on May 5, 2021.

(51) Int. Cl.
*A61K 31/519* (2006.01)
*A61K 39/395* (2006.01)
*A61P 35/00* (2006.01)

(52) U.S. Cl.
CPC ........ *A61K 31/519* (2013.01); *A61K 39/3955* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 9,815,813 B2 | 11/2017 | Chen et al. | |
| 10,077,276 B2 | 9/2018 | Chen et al. | |
| 10,280,171 B2 | 5/2019 | Jones et al. | |
| 10,287,266 B2 | 5/2019 | Chen et al. | |
| 10,561,655 B2 | 2/2020 | Xie et al. | |
| 10,590,090 B2 | 3/2020 | Koltun et al. | |
| 10,858,359 B2 | 12/2020 | Ma et al. | |
| 10,934,285 B2 | 3/2021 | Chen et al. | |
| 10,968,235 B2 | 4/2021 | Chen et al. | |
| 10,988,466 B2 | 4/2021 | Ma et al. | |
| 11,110,171 B2 * | 9/2021 | Mor ................... | G01N 33/6848 |
| 2019/0343836 A1 | 11/2019 | Alghalandis et al. | |
| 2021/0101870 A1 | 4/2021 | Koltun et al. | |
| 2022/0127276 A1 * | 4/2022 | Sun ..................... | C07D 519/00 |
| 2022/0241277 A1 | 8/2022 | Alghalandis et al. | |

FOREIGN PATENT DOCUMENTS

| | | | |
|---|---|---|---|
| AU | 2017276457 B2 | 10/2019 | |
| AU | 2018207464 B2 | 5/2020 | |
| CN | 105916845 A | 8/2016 | |
| CN | 107922388 A | 4/2018 | |
| CN | 109311848 A | 2/2019 | |
| CN | 109415360 A | 3/2019 | |
| WO | 2015107494 A1 | 7/2015 | |
| WO | 2016203406 A1 | 12/2016 | |
| WO | 2017211303 A1 | 12/2017 | |
| WO | WO-2017216706 A1 * | 12/2017 | ......... A61K 31/4545 |
| WO | 2018013597 A1 | 1/2018 | |
| WO | 2018130928 A1 | 7/2018 | |
| WO | 2018172984 A1 | 9/2018 | |
| WO | 2019051084 A1 | 3/2019 | |
| WO | 2019075265 A1 | 4/2019 | |
| WO | 2019126736 A1 | 6/2019 | |
| WO | 2019152454 A1 | 8/2019 | |
| WO | 2019182960 A1 | 9/2019 | |
| WO | 2019199792 A1 | 10/2019 | |
| WO | 2020165733 A1 | 8/2020 | |
| WO | 2020177653 A1 | 9/2020 | |
| WO | 2021061515 A1 | 4/2021 | |

OTHER PUBLICATIONS

Wang et al (SHP2 blockade enhances anti-tumor immunity via tumor cell intrinsic and extrinsic mechanisms, Scientific Reports vol. 11, Article No. 1399, 2021), (Year: 2021).*
Liu et al (Strategies to overcome drug resistance using SHP2 inhibitors, Acta Pharmaceutica Sinica B, vol. 11, Published Online: Mar. 28, 2021), (Year: 2021).*
Chen et al (SHP-2 and PD-L1 Inhibition Combined with Radiotherapy Enhances Systemic Antitumor Effects in an Anti-PD-1-Resistant Model of Non-Small Cell Lung Cancer, Cancer Immunol Res (2020) 8 (7): 883-894) (Year: 2020).*
Berge S.M., et al., "Pharmaceutical Salts," Journal of Pharmaceutical Sciences, Jan. 1977, vol. 66, No. 1, pp. 1-19.
Chinese Search Report for CN Application No. 201910160960.7, mailed Mar. 8, 2021, 2 pages.
Extended European Search Report for European Application No. 20766519.1, mailed Jan. 18, 2023, 12 Pages.
First Office Action for Chinese Application No. 201910160960.7, mailed Mar. 16, 2021, 9 Pages, English Translation.
Guo L., et al., "Puma Mediates the Anti-cancer Effect of Osimertinib In Colon Cancer Cells," OncoTargets and Therapy, Jan. 1, 2017, vol. 10, pp. 5281-5288, DOI: 10.2147/OTT.S139382, XP093004905.
International Preliminary Report on Patentability for International Application No. PCT/CN2020/077391, mailed Sep. 16, 2021, 14 Pages.
International Search Report and Written Opinion for International Application No. PCT/CN2020/077391, mailed Jun. 8, 2020, 26 Pages.
International Search Report and Written Opinion for International Application No. PCT/US2022/027693, mailed Aug. 10, 2022, 13 Pages.
International Search Report and Written Opinion for International Application No. PCT/US2022/027696, mailed Aug. 10, 2022, 13 Pages.

(Continued)

*Primary Examiner* — Laura B Goddard
*Assistant Examiner* — Sarah A Alsomairy
(74) *Attorney, Agent, or Firm* — Eversheds Sutherland (US) LLP

(57) ABSTRACT

Provided herein are combinations that include a SHP2 inhibitor and a PD-1 inhibitor and methods of treating cancer.

31 Claims, 7 Drawing Sheets

(56) References Cited

OTHER PUBLICATIONS

International Search Report and Written Opinion for International Application No. PCT/US2022/027703, mailed Aug. 3, 2022, 10 Pages.
Lamarche M.J., et al., "Identification of TNO155. An Allosteric SHP2 Inhibitor for the Treatment of Cancer," Journal of Medicinal Chemistry, Sep. 1, 2020, vol. 63, No. 22, pp. 13578-13594, DOI: 10.1021/acs.jmedchem.0c01170, XP002803837.
Pai S.I., et al., "Molecular Pathology of Head and Neck Cancer: Implications for Diagnosis, Prognosis, and Treatment," Annual Review of Pathology: Mechanisms of Disease, Annual Reviews, US, Feb. 1, 2009, vol. 4, No. 1, pp. 49-70, DOI: 10.1146/annurev.pathol.4.110807.092158, ISSN 1553-4006, XP093004900.
Partial Supplementary European Search Report for European Application No. 20766519.1, mailed Oct. 25, 2022, 12 Pages.
Eurasian Office Action for Eurasian Patent Application No. 202192383, mailed Aug. 18, 2023, 3 pages.

\* cited by examiner

FIG. 2A

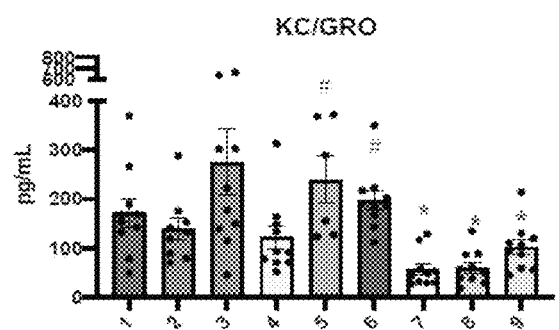

G1: Vehicle
G2: Isotype Control
G3: Anti-PD1
G4: HBI-2376
G5: TNO-155
G6: RMC-4550
G7: HBI-2376+Anti-PD1
G8: TNO-155+Anti-PD1
G9: RMC-4550+Anti-PD1

* Significant compared to G1

FIG. 2B

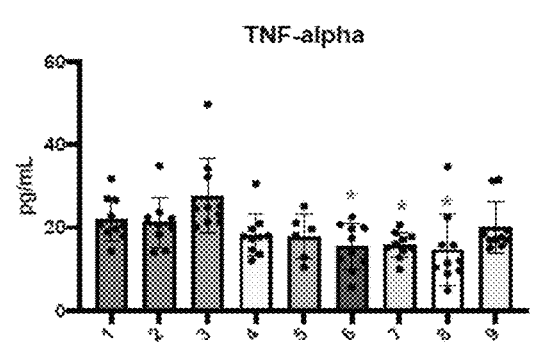

G1: Vehicle
G2: Isotype Control
G3: Anti-PD1
G4: HBI-2376
G5: TNO-155
G6: RMC-4550
G7: HBI-2376+Anti-PD1
G8: TNO-155+Anti-PD1
G9: RMC-4550+Anti-PD1

* Significant compared to G1

FIG. 2C

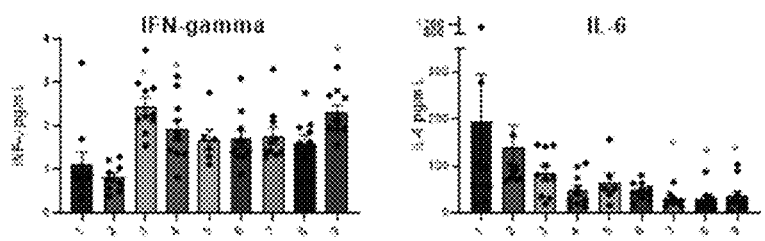

G1: Vehicle
G2: Isotype Control
G3: Anti-PD1
G4: HBI-2376
G5: TNO-155
G6: RMC-4550
G7: HBI-2376+Anti-PD1
G8: TNO-155+Anti-PD1
G9: RMC-4550+Anti-PD1

* Significant compared to G1

Significant compared to G4

COMBINATION THERAPIES COMPRISING SHP2 INHIBITORS AND PD-1 INHIBITORS

CROSS-REFERENCE

This application claims the benefit of U.S. Provisional Application No. 63/184,685 filed May 5, 2021, and U.S. Provisional Application No. 63/320,997 filed Mar. 17, 2022, the contents of which are incorporated herein by reference in their entirety.

FIELD OF THE DISCLOSURE

The present disclosure relates to combinations comprising of a SHP2 and a PD-1 inhibitor; and uses of such combinations in the treatment of cancers.

BACKGROUND OF THE DISCLOSURE

Cancer is a significant cause of morbidity and mortality worldwide. While the standards of care for many different cancer types have greatly improved over the years, current standards of care still fail to meet the need for effective therapies to improve treatment of cancer. Protein tyrosine phosphatase 2 (SHP2) belongs to the protein tyrosine phosphatase family, which is involved in regulating cell proliferation, survival, differentiation, migration and apoptosis. In recent years, SHP2, has been shown to plays an important role in tumor inhibition, especially as the role of SHP2 in tumors has become increasingly clear. Therefore, inhibition of SHP2 has become a feasible anti-tumor strategy.

In the protein tyrosine phosphatase superfamily, SHP2 is the first true proto-oncogene to be confirmed, and it plays an important role in a variety of signaling pathways such as metabolism, differentiation, proliferation, migration and survival. SHP2 can regulate Ras-mitogen-activated protein kinase, Janus kinase-signal transducer and activator of transcription (JAK-STAT) or phosphoinositide 3-kinase-AKT and nuclear factor κB (NF-κB) and other signaling pathways. SHP2 is also the main regulator of the immune checkpoint signaling pathway of programmed cell death protein-1 (PD-1) and B and T lymphocyte attenuation factor (BTLA), which may be related to tumor immunosuppression. In addition, SHP2 mutations rarely occur in tumors.

The clinical use of immune-oncology agents targeting cytotoxic T-lymphocyte-associated protein 4 (CTLA-4) and the programmed cell death receptor-1 (PD-1) and its ligand PD-L1, have resulted in improvements over the standard of care in the treatment of many cancer types. While these checkpoint inhibitors have produced improved clinical responses in such certain cancers, durable clinical responses only occur in approximately 10-45% of patients. Moreover, a significant number of tumors are either resistant or become refractory. Accordingly, there is a need for new therapies, including, for example, combination therapies for the treatment of cancers. Provided herein are combination and methods of treating cancer.

BRIEF SUMMARY

Provided herein, inter alia, are combinations comprising a SHP2 inhibitor and a PD-1 inhibitor.

In an aspect, provided herein is a combination comprising a SHP2 inhibitor compound of Formula (Ia), or a pharmaceutically acceptable salt or solvate thereof:

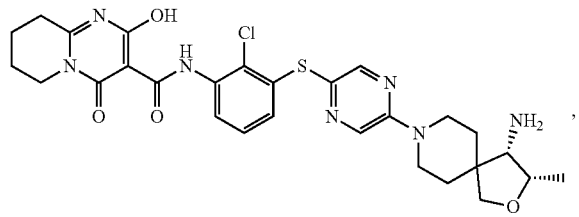

(Ia)

and a PD-1 inhibitor.

In some embodiments, the combination comprises from about 5 mg to about 100 mg of the compound of Formula (Ia), or a pharmaceutically acceptable salt or solvate thereof. In some embodiments, the combination comprises about 5 mg, about 10 mg, about 20 mg, about 30 mg, about 40 mg, or about 50 mg of the compound of Formula (Ia), or a pharmaceutically acceptable salt or solvate thereof.

In some embodiments, the PD-1 inhibitor is a small molecule compound, a nucleic acid, a peptide, a protein, an antibody, a peptibody, a diabody, a minibody, a single-chain variable fragment (ScFv), or a fragment or variant thereof. In some embodiments, the PD-1 inhibitor is an antibody. In some embodiments, the PD-1 antibody is selected from nivolumab, pembrolizumab, pidiluzumab, REGN2810 (also known as SAR-439684), PDR001, SHR-1210, or MEDI0680.

In another aspect, provided herein is a pharmaceutical composition comprising a combination as described herein and a pharmaceutically acceptable excipient.

In another aspect provided herein are methods for preventing and/or treating non-receptor protein tyrosine phosphatase-mediated or dependent diseases or conditions. In some embodiments, provided herein is a method of treating cancer in a subject in need thereof, comprising administering to the patient a combination comprising a therapeutically effective amount of a compound of Formula (Ia), or a pharmaceutically acceptable salt or solvate thereof:

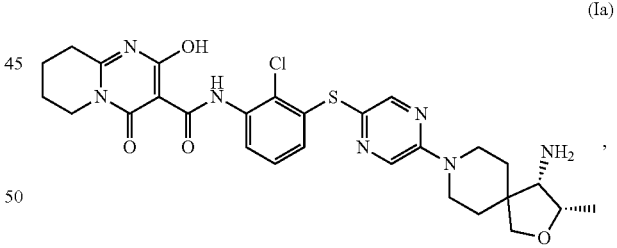

(Ia)

and a therapeutically acceptable amount of a PD-1 inhibitor.

In some embodiments, the compound of Formula (Ia), or a pharmaceutically acceptable salt or solvate thereof, is administered to said patient in need from about 5 mg/kg to about 25 mg/kg. In some embodiments, the compound of Formula (Ia), or a pharmaceutically acceptable salt or solvate thereof is administered to said patient in need at about 5 mg/kg, about 10 mg/kg, about 15 mg/kg, about 20 mg/kg, or about 25 mg/kg.

In some embodiments, the PD-1 inhibitor is a small molecule compound, a nucleic acid, a peptide, a protein, an antibody, a peptibody, a diabody, a minibody, a single-chain variable fragment (ScFv), or a variant thereof. In some embodiments, the PD-1 inhibitor is a PD-1 inhibitor antibody. In some embodiments, the PD-1 antibody is nivolumab, pembrolizumab, pidilizumab, REGN2810 (also known as SAR-439684), PDR001, SHR-1210, or MEDI0680.

In some embodiments, the method comprises administering the compound of Formula (Ia), or a pharmaceutically acceptable salt or solvate thereof; and the PD-1 inhibitor simultaneously or sequentially. In some embodiments, the method comprises administering the compound of Formula (Ia), or a pharmaceutically acceptable salt or solvate thereof; and the PD-1 inhibitor to the patient as a regimen. In some embodiments, the method comprises administering a compound of Formula (Ia), or a pharmaceutically acceptable salt or solvate thereof; and a PD-1 inhibitor to said patient orally or as an intraperitoneal injection. In some embodiments, administration is by intravenous injection (I.V). In some embodiments, the method comprises administering a compound of Formula (Ia), or a pharmaceutically acceptable salt or solvate thereof; and a PD-1 inhibitor to the patient daily. In some embodiments, the method comprises administering a compound of Formula (Ia), or a pharmaceutically acceptable salt or solvate thereof; and a PD-1 inhibitor once a day (QD), twice daily (BID), once a week (QW), twice weekly (BID), three times a week (TIW), or monthly (QM).

In some embodiments, the patient is treatment naïve. In some embodiments, the method comprises administering a compound of Formula (Ia), or a pharmaceutically acceptable salt of solvate thereof; and a PD-1 inhibitor to said patient as a first line therapy. In some embodiments, the method comprises administering a compound of Formula (Ia), or a pharmaceutically acceptable salt or solvate thereof; and a PD-1 inhibitor to the patient as a second, third, fourth, fifth, or sixth line of treatment. In some embodiments, the method comprises administering a compound of Formula (Ia), or a pharmaceutically acceptable salt or solvate thereof; and a PD-1 inhibitor to the patient following treatment with at least one anti-cancer therapy, wherein the anti-cancer therapy is chemotherapy, radiotherapy, surgery, targeted therapy, immunotherapy, or a combination thereof. In some embodiments, the method comprises administering a compound of Formula (Ia), or a pharmaceutically acceptable salt or solvate thereof; and a PD-1 inhibitor to a patient who has failed at least one PD-1 therapy. In some embodiments, the cancer is resistant to at least one anti-cancer agent.

In some embodiments, the cancer is squamous cell carcinoma, nonsquamous cell carcinoma, non-small cell lung cancer (NSCLC), small cell lung cancer, melanoma, hepatocellular carcinoma, renal cell carcinoma, ovarian cancer, head and neck cancer, urothelial cancer, breast cancer, prostate cancer, glioblastoma, colorectal cancer, pancreatic cancer, lymphoma, leiomyosarcoma, liposarcoma, synovial sarcoma, or malignant peripheral sheath tumor (MPNST).

In some embodiments, the method comprises inhibiting metastasis of the cancer in the patient in need of treatment. In some embodiments, the method of treating cancer prolongs the time to disease progression of said cancer in the patient. In some embodiments, the method of treating cancer prolongs the survival of the patient. In some embodiments, the method of treating cancer increases progression-free survival of the patient. In some embodiments, the method of treating cancer reduces a tumor or tumor burden in the patient. In some embodiments, the method reduces or prevent metastasis of a primary tumor in the patient in need.

In another aspect, presented herein is a method of modulating one or more biomarkers (cytokines) selected from TNF-α, INF-γ, IL-1β, IL-2, IL-4, IL-5, IL-6, IL-10, IL-12p70, and KC/GRO (CXCL1). In some embodiments, the one or more biomarkers increased or lowered over baseline levels. In some embodiments, the one or more biomarkers is lowered or increased by at least 5%, at least 10%, at least 15%, at least 20%, at least 25%, at least 30%, at least 40%, at least 50%, at least 100%, or at least 150%. In some embodiments, the one or more biomarkers in is lowered or increased by at least 1.5 times, 2 times, 3 times, 4 times, 5 times, 10 times, 15 times, 20 times, or 25 times.

Other objects, features and advantages of the combinations and methods described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below.

FIGS. 2A, 2B and 2C show Keratinocyte chemoattractant (KC)/human growth-regulated oncogene (GRO), TNF-α, IFN-γ and IL-6 expression levels in tumor (MC38) after various combination treatments.

DETAILED DESCRIPTION

Combinations

Figure 1A:
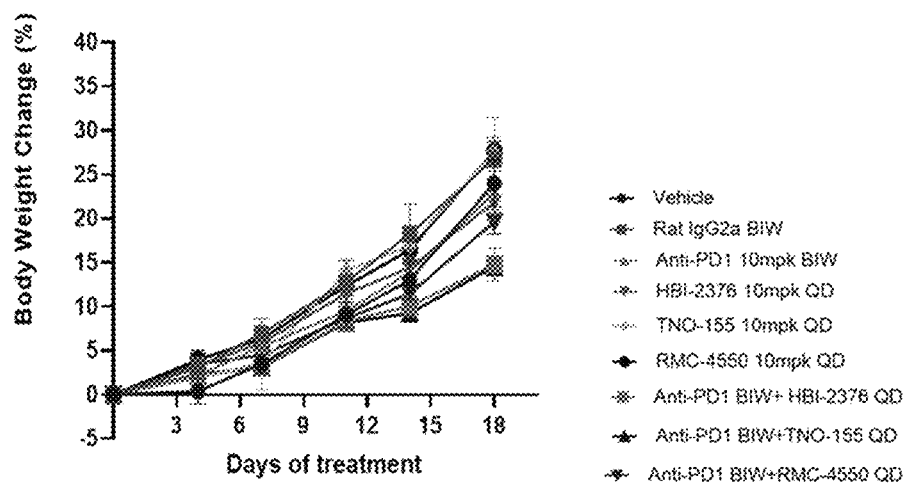
FIGS. 1A and 1B display results of an efficacy study in mice after administration with various combinations, including the combinations described herein.

In one aspect, described herein are combinations (e.g., combination therapies, such as therapeutic methods and uses, kits and compositions) for treating cancer. In some embodiments, the combinations described herein comprise a SHP2 inhibitor and a PD-1 inhibitor. In some embodiments, the SHP2 inhibitor is a pyrazine derivative. In some embodiments, a combination may comprise a first pharmaceutical composition and a second pharmaceutical composition. In some embodiments, the first pharmaceutical composition comprises a SHP2 inhibitor and the second pharmaceutical composition comprises a PD-1 inhibitor. In some embodiments, the first pharmaceutical composition and the second pharmaceutical composition are co-packaged as a kit, which may further include instructions for co-administration of the first and second pharmaceutical compositions. In some embodiments, the first and second compositions may be packaged separately for combination in a clinical setting by administering them to a patient within a time frame during which the patient derives clinical benefit from the first pharmaceutical composition and the second pharmaceutical composition at the same time. In some embodiments, a combination may comprise a pharmaceutical composition comprising a SHP2 inhibitor and a PD-1 inhibitor. In some embodiments, a combination comprises a unit dosage form of a pharmaceutical composition comprising a SHP2 inhibitor and a PD-1 inhibitor. In some embodiments, a combination comprises a first pharmaceutical composition comprising a SHP2 inhibitor for use in the treatment of cancer in combination with a second pharmaceutical composition comprising a PD-1 inhibitor. In some embodiments, a combination comprises a use of a SHP2 inhibitor for preparation of a first pharmaceutical composition for use in the treatment of cancer in combination with a second pharmaceutical composition comprising a PD-1 inhibitor.

In some embodiments, described herein is a combination comprising:

(i) a therapeutically effective amount of a SHP2 inhibitor having the structure of Formula (I), or a pharmaceutically acceptable salt or solvate thereof:

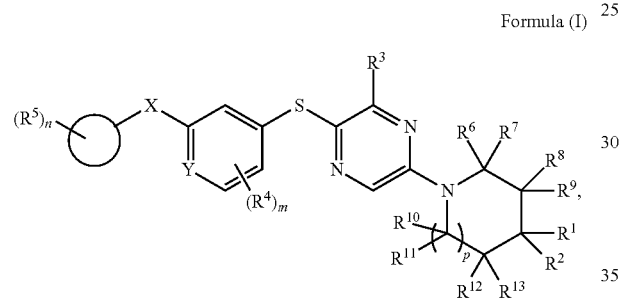

Formula (I)

wherein, $R^1$ and $R^2$ are each the same or different, and they are each independently selected from H, D, halogen, —CN, —C(O)OH, —CHO, —OH, —NO$_2$, and the following substituted or unsubstituted groups: —NH$_2$, $C_1$-$C_{10}$ alkyl, $C_1$-$C_{10}$ alkylamino, $C_1$-$C_{10}$ alkoxy, $C_3$-$C_{12}$ cycloalkyl, $C_3$-$C_{12}$ cycloalkyloxy, 3-12 membered heterocyclic group, $C_6$-$C_{10}$ aryl group, 5-10 membered heteroaryl group; or $R^1$ and $R^2$ form a 3-8 membered saturated or unsaturated cycloalkyl or heterocyclic group, optionally, the 3-8 membered saturated or unsaturated cycloalkyl or heterocyclic group has one to three —OH, —NH$_2$, —CN, NO$_2$, halogen, $C_1$-$C_{10}$ alkyl, $C_1$-$C_{10}$ alkaneoxy, $C_1$-$C_{10}$ alkylamino, $C_3$-$C_{12}$ cycloalkyl, $C_6$-$C_{10}$ aryl or 5-10 membered heteroaryl;

$R^3$ is selected from H, D, or —NH$_2$;

X is selected from a bond, —NH—, or —C(O)NH—;

Y is selected from N or $CR^{13}$, wherein $R^{13}$ is selected from H, D, —OH, —CN, halogen, $C_1$-$C_{10}$ alkyl group, $C_1$-$C_{10}$ alkoxy, $C_3$-$C_{12}$ cycloalkane amino, $C_1$-$C_{10}$ alkylamino, $C_3$-$C_{12}$ cycloalkyl, 3-8 membered heterocyclic group, halogenated $C_1$-$C_{10}$ alkylamino, or $C_6$-$C_{10}$ aryl or 5-10 membered heteroaryl group, the heterocyclic group or heteroaryl group optionally contains one to four heteroatoms, and the heteroatoms are selected from S, O, N or —NH—;

each $R^4$ is the same or different, and is independently selected from H, D, halogen, —CN, —C(O)OH, —CHO, —OH, —NO$_2$, —C(O)NHR$^{14}$ or —NHC (O)R$^{15}$, substituted or unsubstituted with the following groups: —NH$_2$, $C_1$-$C_{10}$ alkyl, $C_1$-$C_{10}$ alkylamino, $C_1$-$C_{10}$ alkoxy, $C_3$-$C_{12}$ cycloalkyl, 3-12 membered heterocyclic group, $C_6$-$C_{10}$ aryl, or 5-10 membered heteroaryl; wherein $R^{14}$ and $R^{15}$ are each independently selected from $C_1$-$C_{10}$ alkylamino, $C_3$-$C_{12}$ cycloalkyl, $C_6$-$C_{10}$ aryl or 5-10 membered heteroaryl; the substitution is selected from $C_1$-$C_{10}$ alkyl, halogen atom, —NH$_2$, —CN, —C(O)OH, —CHO, —OH, —NO$_2$, $C_1$-$C_{10}$ alkoxy, $C_1$-$C_{10}$ alkylamino, $C_3$-$C_{12}$ cycloalkyl, $C_6$-$C_{10}$ aryl, 5-10 membered heteroaryl or 3-12 membered heterocyclic group is substituted by one or more substituents, the above-mentioned substituents are optionally substituted with one to three substituents selected from $C_1$-$C_{10}$ alkyl, halogen, —NH$_2$, —CN, —C(O)OH, —CHO, —OH, —NO$_2$, $C_1$-$C_{10}$ alkoxy, $C_1$-$C_{10}$ alkylamino, or $C_3$-$C_{12}$ cycloalkyl;

is selected from $C_6$-$C_{10}$ aryl, 5-10 membered heteroaryl, $C_4$-$C_{12}$ cycloalkyl, 3-12 membered heterocyclic group, $C_6$-$C_{14}$ bridged ring group or spiro ring group, or $C_6$-$C_{14}$ bridged heterocyclic group or spiro heterocyclic group; wherein the 5-10 membered heteroaryl, 3-12 membered heterocyclic group, $C_6$-$C_{14}$ bridged heterocyclic group or spiro heterocyclic group contains one to three heteroatoms or groups selected from N, —NH—, 0, S, C(O), or S(O);

each $R^5$ is the same or different, and is independently selected from H, D, halogen, —CN, —C(O)OH, —CHO, —OH, —NO$_2$, aminoacyl, substituted or unsubstituted following groups: $C_1$-$C_{10}$ alkyl, $C_1$-$C_{10}$ alkylamino, $C_1$-$C_{10}$ alkoxy, —NH$_2$, $C_3$-$C_{12}$ cycloalkyl, 3-12 membered heterocyclic group, $C_6$-$C_{10}$ aryl or 5-10 membered heteroaryl, the substitution is selected from $C_1$-$C_{10}$ alkyl, $C_3$-$C_{12}$ cycloalkyl, 3-12 membered heterocyclic group, halogen, —NH$_2$, —CN, —C(O)OH, —CHO, —OH, —NO$_2$, hydroxy-$C_1$-$C_{10}$ alkyl, $C_1$-$C_{10}$ alkoxy, $C_1$-$C_{10}$ alkylamino, 5-10 membered heteroaromatic group, $C_6$-$C_{10}$ aryl group or 3-12 membered heterocyclic group substituted by one or more substituents; or any two adjacent $R^5$ form a 3-6 membered saturated or unsaturated ring, and optionally the 3-6 membered saturated or unsaturated ring is substituted with one to three —OH, —NH$_2$, —CN, halogen, $C_1$-$C_{10}$ alkyl, $C_1$-$C_{10}$ alkoxy, $C_3$-$C_{12}$ cycloalkylamino, $C_1$-$C_{10}$ alkylamino, $C_3$-$C_{12}$ cycloalkyl, halogenated $C_1$-$C_{10}$ alkylamino, $C_6$-$C_{10}$ aryl or 5-10 member heteroaryl;

$R^6$, $R^7$, $R^8$, $R^9$, $R^{10}$, $R^{11}$, $R^{12}$, and $R^{13}$ are each independently selected from H, D, halogen, —CN, —C(O)OH, —CHO, —OH, —NO$_2$, substituted or unsubstituted the group selected from —NH$_2$, $C_1$-$C_{10}$ alkyl, $C_1$-$C_{10}$ alkylamino, $C_1$-$C_{10}$ alkoxy, $C_3$-$C_{12}$ cycloalkyl, $C_3$-$C_{12}$ cycloalkyloxy group, 3-12 membered heterocyclic group, $C_6$-$C_{10}$ aryl, and 5-10 membered heteroaryl, the substitution is selected from $C_1$-$C_{10}$ alkyl, $C_3$-$C_{12}$ cycloalkyl, 3-12 membered heterocyclic group, halogen, —NH$_2$, —CN, —C(O)OH, —CHO, —OH, —NO$_2$, hydroxy-$C_1$-$C_{10}$ alkyl, $C_1$-$C_{10}$ alkoxy, $C_1$-$C_{10}$ alkylamino, 5-10 membered heteroaryl or $C_6$-$C_{10}$ aryl;

m is 0, 1, 2 or 3;

n is 0, 1, 2 or 3; and p is 0, 1, or 2; and (ii) a therapeutically effective amount of a PD-1 inhibitor.

In some embodiments, the compound of Formula (I) has the structure of Formula (II), or a pharmaceutically acceptable salt or solvate thereof:

Formula (II)

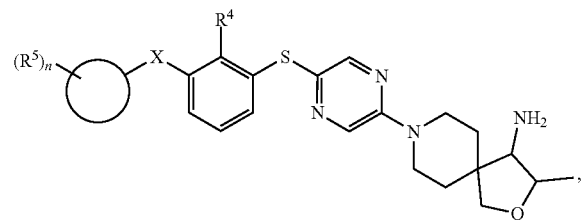

wherein,

X is selected from chemical bond, —NH—, —CONH—;

$R^4$ is selected from H, D, halogen atom, —CN, —C(O)OH, —CHO, —OH, —NO$_2$, —C(O)NHR$^{14}$ or —NHC(O)R$^{15}$, substituted or unsubstituted with the group selected from —NH$_2$, $C_1$-$C_{10}$ alkyl, $C_1$-$C_{10}$ alkylamino, $C_1$-$C_{10}$ alkoxy, $C_3$-$C_{12}$ cycloalkyl, 3-12 membered heterocyclic group, $C_6$-$C_{10}$ aryl, or 5-10 membered heteroaryl; wherein $R^{14}$ and $R^{15}$ are each independently selected from $C_1$-$C_{10}$ alkylamino, $C_3$-$C_{12}$ cycloalkyl, $C_6$-$C_{10}$ aryl or 5-10 membered heteroaryl group; the substituent is selected from $C_1$-$C_{10}$ alkyl, halogen, —NH$_2$, —CN, —C(O)OH, —CHO, —OH, —NO$_2$, or $C_1$-$C_{10}$ alkoxy, substituted by one or more substituents of $C_1$-$C_{10}$ alkylamino, $C_3$-$C_{12}$ cycloalkyl, $C_6$-$C_{10}$ aryl, 5-10 membered heteroaryl, or 3-12 membered heterocyclic group, the substituents are optionally selected from $C_1$-$C_{10}$ alkyl, halogen, —NH$_2$, —CN, —C(O)OH, —CHO, —OH, —NO$_2$, $C_1$-$C_{10}$ alkoxy, $C_1$-$C_{10}$ alkylamino, or $C_3$-$C_{12}$ cycloalkyl;

is selected from $C_6$-$C_{10}$ aryl, 5-10 membered heteroaryl, $C_4$-$C_{12}$ cycloalkyl, 3-12 membered heterocyclic group, $C_6$-$C_{14}$ bridged ring group or spiro ring group, or $C_6$-$C_{14}$ bridged heterocyclic group or spiro heterocyclic group; wherein the 5-10 membered heteroaryl group, 3-12 membered heterocyclic group, $C_6$-$C_{14}$ bridged heterocyclic group or spiro heterocyclic group contains one to three heteroatom or groups selected from N, —NH—, O, S, C(O), or S(O);

each $R^5$ is the same or different, and is independently selected from H, D, halogen atom, —CN, —C(O)OH, —CHO, —OH, —NO$_2$, or aminoacyl, substituted or unsubstituted with the group selected from $C_1$-$C_{10}$ alkyl, $C_1$-$C_{10}$ alkylamino, $C_1$-$C_{10}$ alkoxy, —NH$_2$, $C_3$-$C_{12}$ cycloalkyl, 3-12 membered heterocyclic group, $C_6$-$C_{10}$ aryl or 5-10 membered heteroaryl, the substituent selected from $C_1$-$C_{10}$ alkyl, $C_3$-$C_{12}$ cycloalkyl, 3-12 membered heterocyclic group, halogen, —NH$_2$, —CN, —C(O)OH, —CHO, —OH, —NO$_2$, hydroxy-$C_1$-$C_{10}$ alkyl, $C_1$-$C_{10}$ alkoxy, $C_1$-$C_{10}$ alkylamino, 5-10 membered heteroaromatic group, $C_6$-$C_{10}$ aryl or 3-12 membered heterocyclic group substituted by one or more substituents; or any two adjacent $R^5$ form a 3-6 membered saturated or unsaturated ring, and is optionally, the 3-6 membered saturated or unsaturated ring is comprises one to three —OH, —NH$_2$, —CN, halogen, $C_1$-$C_{10}$ alkyl, $C_1$-$C_{10}$ alkoxy, $C_3$-$C_{12}$ cycloalkylamino, $C_1$-$C_{10}$ alkylamino, $C_3$-$C_{12}$ cycloalkyl, halogenated $C_1$-$C_{10}$ alkylamino, $C_6$-$C_{10}$ aryl or 5-10 member heteroaryl; and n is 0, 1, 2 or 3.

In some embodiments, $R^4$ is selected from H, D, halogen, —CN, unsubstituted or halogen atom substituted $C_1$-$C_{10}$ alkyl.

In some embodiments,

is elected from phenyl, naphthyl, 5-10 membered heteroaryl or 3-12 membered heterocyclic group; wherein the 5-10 membered heteroaryl group and 3-12 membered heterocyclic group contain one to three heteroatoms or groups optionally selected from N, NH, O, S, or C(O).

In some embodiments, the 5-10 membered heteroaromatic ring is selected from thienyl; pyridyl; pyrimidinyl; pyrazinyl; pyridazinyl; pyrrolyl; pyrazolyl; thiazolyl; 1,2,3-triazolyl; 1,2,4-triazoly; imidazolyl; tetrazolyl; isothiazolyl; oxazolyl; isoxazolyl; thiadiazolyl; oxadiazolyl; benzothienyl; indolyl; benzimidazolyl; benzothiazolyl; benzofuranyl; quinolinyl; isoquinolinyl; quinazolinyl; indazolyl; indole[1,2-a]pyrazinyl; 4,7-diazaindole; pyrazolopyrimidinyl; imidazopyrimidinyl; oxazolopyrimidinyl; isoxazopyrimidiny; imidazopyrazinyl; pyrazolopyrazinyl; pyrrolopyrazinyl; or furan. In some embodiments, any one of pyrazinyl, thienopyrazinyl, pyridopyrimidinone, benzoxazolyl, and benzothiazolyl; the 3-12 membered heterocyclic group is selected from aziridinyl, oxetanyl, pyrrolidinyl, tetrahydrofuranyl, tetrahydrothienyl, piperidinyl, morpholinyl, piperazinyl, thiomorpholinyl, tetrahydropyranyl, 1,1-dioxythiomorpholinyl, butyrolactam, valerolactam, caprolactam, butyrolactone, valerolactone, caprolactone, succinimide or

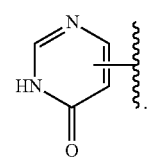

In some embodiments, the 3-12 membered heterocyclic group is selected from butyrolactamyl, pyrrolidinyl, succinimide, or

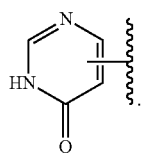

In some embodiments, each $R^5$ is the same or different, and is independently selected from H, D, halogen, —CN, —C(O)OH, —CHO, —OH, —NO$_2$, aminoacyl, substituted or unsubstituted with a $C_1$-$C_{10}$ alkyl, $C_1$-$C_{10}$ alkylamino, $C_1$-$C_{10}$ alkoxy, —NH$_2$, and the substitution is selected from $C_1$-$C_{10}$ alkyl, halogen, —NH, —CN, —OH, —NO$_2$ are substituted by one or more substituents; or any two adjacent $R^5$ form a 3-6 membered saturated or unsaturated ring, optionally, the 3-6-membered saturated or unsaturated ring is substituted with one to three —OH, —NH$_2$, —CN, halogen, $C_1$-$C_{10}$ alkyl, and $C_1$-$C_{10}$ alkoxy.

In some embodiments, the compound of Formula (I) has the structure of Formula (Ia), or a pharmaceutically acceptable salt or solvate thereof:

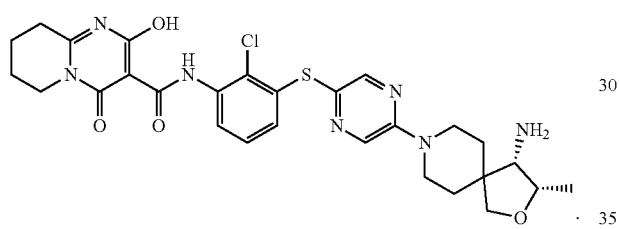

(Ia)

In some embodiments, the compound of Formula (I) or (Ia) is N-(3-((5-((3S,4S)-4-amino-3-methyl-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide, or a pharmaceutically acceptable salt or solvate thereof.

In some embodiments, the compound of Formula (I), (Ia), or (II), or a pharmaceutically acceptable salt thereof is a SHP2 inhibitor. The compound of Formulas (I), (Ia) and (II) are substantially described by International Patent Application No. PCT/CN2020/077391, filed Mar. 2, 2020, which is incorporated herein by reference in its entirety.

In some embodiments, described herein is a combination comprising:

(i) a therapeutically effective amount of a SHP2 inhibitor having the structure of Formula (III), or a pharmaceutically acceptable salt or solvate thereof:

Formula (III)

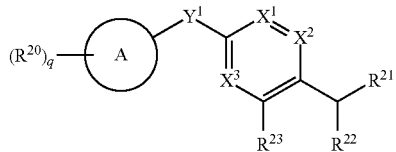

wherein,
$X^1$ is N or CH;
$X^2$ is N or CH;
$X^3$ is N or CH;
wherein at least one of X1, X2, or X3 is N;
$Y^1$ is S or direct bond;
A is selected from the group consisting of 5- to 12-membered monocyclic or polycyclic cycloalkyl, monocyclic or polycyclic heterocycloalkyl, monocylic or polycyclic aryl, or polycyclic heteroaryl;
$R^{20}$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^{25}$, halogen, —NO$_2$, —CN, —NR$^{24}$R$^{25}$, —SR$^{24}$, —S(O)$_2$NR$^{24}$R$^{25}$, —S(O)$_2$R$^{24}$, —NR$^{24}$S(O)$_2$NR$^{24}$R$^{25}$, —NR$^{24}$S(O)$_2$R$^{25}$, —S(O)NR$^{24}$R$^{24}$, —S(O)R$^{24}$, —NR$^{24}$S(O)NR$^{24}$R$^{25}$, —NR$^{24}$S(O)R$^{25}$, —C(O)R$^{24}$, —CO$_2$R$^{24}$, —C(O)NR$^{24}$R$^{25}$, —NR$^{24}$CO)R$^{25}$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —NO$_2$, oxo, —CN, —R$^{24}$, —OR$^{24}$, —NR$^{24}$R$^{25}$, —SR$^{24}$, —S(O)$_2$NR$^{24}$R$^{25}$, —S(O)$_2$R$^{24}$, —NR$^{24}$S(O)$_2$NR$^{24}$R$^{25}$, —NR$^{24}$S(O)$_2$R$^{25}$, —S(O)NR$^{24}$R$^{25}$, —S(O)R$^2$, —NR$^{24}$S(O)NR$^{24}$R$^{25}$, —NR$^{24}$S(O)R$^5$, heterocycle, aryl, or heteroaryl;
$R^{21}$ and $R^{22}$ are independently selected from the group consisting of —H, -D, —OH, —C$_1$-C$_6$alkyl, a 3- to 12-membered monocyclic or polycyclic heterocycle, a 5- to 12-membered spiroheterocycle, C$_3$-C$_8$cycloalkyl, —(CH$_2$)$_q$—R$^{28}$, or —(CH$_2$)$_q$C(O)NR$^{24}$R$^{25}$, wherein each alkyl, heterocycle, or cycloalkyl is optionally substituted with one or more —C$_1$-C$_6$alkyl, —OH, —NH$_2$, —OR$^{28}$, —NHR$^{28}$, (CH$_2$)$_q$OH, heterocyclyl, or spiroheterocyclyl;
or $R^{22}$ can combine with $R^{21}$ to form a 3- to 12-membered monocyclic or polycyclic heterocycle, or a 5- to 12-membered spiroheterocycle, wherein each heterocycle or spiroheterocycle is optionally substituted with one or more —C$_1$-C$_6$alkyl, halogen, —OH, —OR, —NHR$^{28}$, optionally substituted heteroaryl, optionally substituted heterocyclyl, —(CH$_2$)$_q$NH$_2$, —(CH$_2$)$_q$OH, —COOR$^{28}$, —CONHR$^{28}$, —CONH(CH$_2$)$_q$COOR$^{28}$, —NHCOOR$^{28}$, —O—C(O)—NR$^{24}$R$^{25}$, —CF$_3$, —CHF$_2$, —CH$_2$F, or =O; wherein the heteroaryl and heterocyclyl are optionally substituted with —CN;
$R^{23}$ is —C$_1$-C$_6$alkyl, —C$_1$-C$_6$haloalkyl, —C$_1$-C$_6$hydroxyalkyl —CF$_2$OH, —CHFOH, —NH—NHR$^{24}$, —NH—OR$^{24}$, —O—NR$^{24}$R$^{25}$, —NHR$^{24}$, —OR$^{24}$, —NHC(O)R$^{24}$, —NHC(O)NHR$^{24}$, —NHS(O)$_2$R$^{24}$, —NHS(O)$_2$NHR$^{24}$, —S(O)$_2$OH, —C(O)OR$^{24}$, —NH(CH$_2$)$_n$OH, —C(O)NH(CH$_2$)$_n$OH, —C(O)NH(CHI)$_q$R$^{28}$, —C(O)R$^{28}$, —NH2, —OH, —CN, —C(O)NR$^{24}$R$^{25}$, —S(O)$_2$NR$^{24}$R$^{25}$, C$_3$-C$_8$cycloalkyl, aryl, heterocyclyl containing 1-5 heteroatoms selected from the group consisting of N, S, P. and O, or heteroaryl containing 1-5 heteroatoms selected from the group consisting of N, S, P, and O, wherein each alkyl, cycloalkyl, or heterocyclyl is optionally substituted with one or more —OH, —NH$_2$, —OR, halogen, or oxo; wherein each aryl or heteroaryl is optionally substituted with one or more —OH, —NH$_2$, or halogen;
$R^{24}$ and $R^{25}$ are each independently, at each occurrence, selected from the group consisting of —H, -D, —C$_1$-C$_6$alkyl, —C$_2$-C$_6$alkenyl, —C$_3$-C$_8$cycloalkenyl, —C$_2$-C$_6$alkynyl, —C$_3$-C$_8$cycloalkyl, a monocyclic or polycyclic 3- to 12-membered heterocycle, —OR$^{26}$, —SR$^{26}$, halogen, —NR$^{26}$R$^{27}$, —NO$_2$, and —CN;

R$^{26}$ and R$^{27}$ are independently, at each occurrence. —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

R$^{28}$ is independently —H, -D, —C$_1$-C$_6$alkyl, —C$_1$-C$_6$cycloalkyl, —C$_2$-C$_6$alkenyl, —(CH$_2$)$_q$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_q$-aryl is optionally substituted with one or more —OH, halogen, —NO$_2$, oxo, —CN, —R$^{24}$, —OR$^{24}$, —NR$^{24}$R$^{25}$, —SR$^{24}$, —S(O)$_2$NR$^{24}$R$^{25}$, —S(O)$_2$R$^{25}$, —NR$^{24}$S(O)$_2$NR$^{24}$R$^{25}$, —NR$^{24}$S(O)$_2$R$^{25}$, —S(O)NR$^{24}$R$^{25}$, —S(O)R$^{24}$, —NR$^{24}$S(O)NR$^{24}$R$^{25}$, —NR$^{24}$S(O)R$^{25}$, —C(O)NR$^{24}$R$^{25}$—, —NR$^{24}$R$^{25}$C(O)—, heterocycle, aryl, heteroaryl, —(CH$_2$)$_q$OH, —C$_1$-C$_6$alkyl, CF$_3$, CHF$_2$, or CH$_2$F; and q is independently 0, 1, 2, 3, 4, 5, 6, 7, 8, 9, or 10; and (ii) a therapeutically effective amount of a PD-1 inhibitor.

In some embodiments, the compound of Formula (IIIa), or a pharmaceutically acceptable salt of solvate thereof:

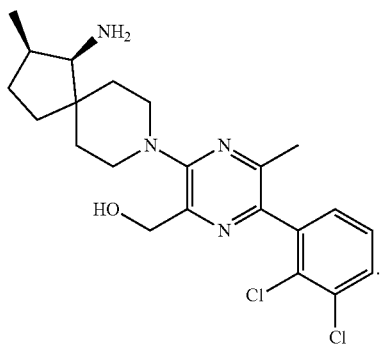

Formula (IIIa)

In some embodiments, the compound of Formula (IIIa) is RMC-4550 or a pharmaceutically acceptable salt or solvate thereof. In some embodiments, the SHP2 inhibitor is a compound described in PCT/US2018/055502 filed on Oct. 11, 2018, which is herein incorporated by reference in its entirety.

In some embodiments, described herein is a combination comprising:

(i) a therapeutically effective amount of a SHP2 inhibitor having the structure of Formula (IV), or a pharmaceutically acceptable salt or solvate thereof:

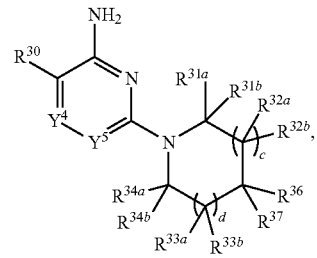

Formula (IV)

wherein
  c is selected from 0 and 1;
  d is selected from 0 and 1;
  Y$^4$ is selected from CH and N;
  Y$^5$ is selected from CR$^{35}$ and N;
  R$^{30}$ is —X$^5$R$^{30a}$; wherein
    R$^{30a}$ is selected from C$_{6-10}$aryl, C$_{3-8}$cycloalkyl, C$_{3-8}$Cycloalkenyl and a 5-9 member heteroaryl group containing from 1 to 4 heteroatoms or groups independently selected from N, —C(O)—, O and S; wherein said aryl or heteroaryl of R$^{30a}$ is substituted with 1 to 5 R$^{38}$ groups independently selected from halo, amino, hydroxy, N$_3$, C$_{1-4}$alkyl, dimethyl-amino, hydroxy-substituted-C$_{1-4}$alkyl, halo-substituted-C$_{1-4}$alkyl, amino-substituted-C$_{1-4}$alkyl, —C(O)OR$^{40}$ and —NHC(O)R$^{40}$; and
    X is selected from a bond, S(O)$_{m1}$, O, C(O), COR$^{40}$, CR$^{39a}$R$^{39b}$, NR$^{40}$; wherein
      m1 is selected from 0, 1 and 2;
      each R$^{39a}$ and R$^{39b}$ is independently selected from halo and C$_{1-4}$alkyl; and
      R$^{40}$ is selected from hydrogen and C$_{1-4}$alkyl;
  R$^{31}$ and R$^{31a}$ are independently selected from hydrogen, C$_{1-4}$alkyl, C$_{1-4}$ alkoxy, amino, hydroxy, C$_{3-8}$cycloalkyl and C$_{1-4}$ alkyl-amino;
  R$^{32}$ and R$^{32a}$ are independently selected from halo, carbonyl, C$_{1-4}$alkyl, C$_{1-4}$alkoxy, amino, hydroxy, C$_{3-8}$cycloalkyl and C$_{1-4}$ alkyl-amino;
  R$^{33}$ and R$^{33a}$ are independently selected from hydrogen, halo, carbonyl, C$_{1-4}$alkyl, C$_{1-4}$alkoxy, amino, hydroxy, C$_{3-8}$Cycloalkyl and C$_{1-4}$alkyl-amino;
  R$^{34}$ and R$^{34a}$ are independently selected from hydrogen, carbonyl, C$_{1-4}$alkyl, C$_{1-4}$ alkoxy, amino, hydroxy, C$_{3-8}$cycloalkyl and C$_{1-4}$ alkyl-amino;
  wherein any two groups selected from R$^{31}$, R$^{31a}$, R$^{32}$, R$^{32a}$, R$^{33}$, R$^{33a}$, R$^{34}$, R$^{34a}$ and R$^{36}$ can form a 5 to 6 member unsaturated or partially saturated ring;
  R$^{35}$ is selected from hydrogen, halo, cyano, C$_{1-4}$ alkyl, C$_{1-4}$alkoxy, amino-carbonyl, halo-substituted C$_{1-4}$ alkyl, halo-substituted C$_{1-4}$ alkoxy, hydroxy-substituted C$_{1-4}$ alkyl, amino-substituted C$_{1-4}$alkyl, —S(O)$_{1-2}$R$^{35a}$, —C(S)R$^{35b}$, —C(O)NR$^{35a}$R$^{35b}$, and —NR$^{35a}$C(O)R$^{35b}$; wherein R$^{35a}$ and R$^{35b}$ are independently selected from hydrogen and C$_{1-4}$ alkyl;
  R$^{36}$ and R$^{37}$ together with the carbon atom to which they are both attached form a 3 to 7 member saturated or partially unsaturated ring that can optionally contain 1 to 3 heteroatoms or groups independently selected from N, C(O), O and S(O)$_{m1}$; wherein m1 is selected from 0, 1 and 2; wherein said saturated ring formed by R$^{36}$ and R$^{37}$ can be unsubstituted or substituted with 1 to 3 groups independently selected from amino, hydroxy, methoxy, halo, methyl, methyl-amino and isobutyryloxy; and (ii) a therapeutically effective amount of a PD-1 inhibitor.

In some embodiments, the structure of Formula (IVa), or a pharmaceutically acceptable salt or solvate thereof is:

Formula (IVa)

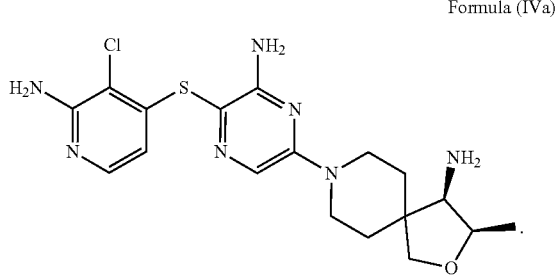 [SMILES: C[C@H]1OCC2(CCN(c3cnc(Sc4ccnc(N)c4Cl)c(N)n3)CC2)[C@H]1N]

In some embodiments, the compound of Formula (IVa) is TNO-155 or a pharmaceutically acceptable salt or solvate thereof. In some embodiments, the SHP2 inhibitor is any of the compounds disclosed in PCT/IB2015/050345 filed Jan. 16, 2015, which is herein incorporated by reference in its entirety.

Any combination of the groups described above for the various variables is contemplated herein. Throughout the specification, groups and substituents thereof are chosen by one skilled in the field to provide stable moieties and compounds.

In some embodiments, the combination comprises a compound disclosed herein, or a pharmaceutically acceptable salt or solvate thereof (e.g., Formula (Ia)) present at an amount of greater than about 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 85 mg, 90 mg, 100 mg, 125 mg, 150 mg, 175 mg, or 200 mg. In some embodiments, the compound disclosed herein is present in an amount greater than about 5 mg or about 10 mg. In some embodiments, the composition comprises a compound of disclosed herein) in an amount from about 1 mg to about 500 mg. In some embodiments, the composition comprises a compound disclosed herein in an amount from about 1 mg to about 10 mg, from about 1 mg to about 25 mg, from about 1 mg to about 50 mg, from about 5 mg to about 10 mg, from about 5 mg to about 25 mg, from about 5 mg to about 50 mg, from about 10 mg to about 25 mg, from about 10 mg to about 50 mg, from about 50 mg to about 100 mg, from about 100 mg to about 200 mg, or from about 200 mg to about 500 mg.

In some embodiments, the combination comprises at least about 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 85 mg, 90 mg, 100 mg, 125 mg, 150 mg, 175 mg, or 200 mg of the compound disclosed herein, or a pharmaceutically acceptable salt or solvate thereof (e.g., compound of Formula (Ia)). In some embodiments, the combination comprises at least about 1 mg, 2 mg, 3 mg, 4 mg, 5 mg, 6 mg, 7 mg, 8 mg, 9 mg, or 10 mg of the compound disclosed herein. In some embodiments, the compound disclosed herein is present in the composition in an amount of at least about 5 mg or about 10 mg. In some embodiments, the combination comprises at least about 1 mg to about 10 mg, about 1 mg to about 25 mg, about 1 mg to about 50 mg, about 5 mg to about 10 mg, about 5 mg to about 25 mg, about 5 mg to about 50 mg, about 10 mg to about 25 mg, about 10 mg to about 50 mg, about 50 mg to about 100 mg, or about 100 mg to about 200 mg of the compound disclosed herein.

In some embodiments, the combination comprises from about 5 mg to about 500 mg or from about 5 mg to about 100 mg of the compound disclosed herein, or a pharmaceutically acceptable salt or solvate thereof (e.g., a compound of Formula (Ia)). In some embodiments, the combination comprises about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, or about 200 mg of the compound disclosed herein.

In some embodiments, the combination comprises a compound disclosed herein, or a pharmaceutically acceptable salt or solvate thereof (e.g., Formula (Ia)) in an amount relative to the weight of the patient (i.e., mg/kg). In some instances, the compound disclosed herein is present in an amount equivalent to about: 0.0001 mg/kg to about 200 mg/kg, 0.001 mg/kg to about 200 mg/kg, 0.01 mg/kg to about 200 mg/kg, 0.01 mg/kg to about 150 mg/kg, 0.01 mg/kg to about 100 mg/kg, 0.01 mg/kg to about 50 mg/kg, 0.01 mg/kg to about 25 mg/kg, 0.01 mg/kg to about 10 mg/kg, or 0.01 mg/kg to about 5 mg/kg, 0.05 mg/kg to about 200 mg/kg, 0.05 mg/kg to about 150 mg/kg, 0.05 mg/kg to about 100 mg/kg, 0.05 mg/kg to about 50 mg/kg, 0.05 mg/kg to about 25 mg/kg, 0.05 mg/kg to about 10 mg/kg, or 0.05 mg/kg to about 5 mg/kg, 0.5 mg/kg to about 200 mg/kg, 0.5 mg/kg to about 150 mg/kg, 0.5 mg/kg to about 100 mg/kg, 0.5 mg/kg to about 50 mg/kg, 0.5 mg/kg to about 25 mg/kg, 0.5 mg/kg to about 10 mg/kg, or 0.5 mg/kg to about 5 mg/kg. In other instances the compound disclosed herein, is present in an amount equivalent to about 1 mg/kg to about 200 mg/kg, 1 mg/kg to about 150 mg/kg, 1 mg/kg to about 100 mg/kg, 1 mg/kg to about 50 mg/kg, 1 mg/kg to about 25 mg/kg, 1 mg/kg to about 10 mg/kg, or 1 mg/kg to about 5 mg/kg.

In some embodiments, the combination comprises from about 5 mg/kg to about 25 mg/kg per patient body weight of a compound disclosed herein, or a pharmaceutically acceptable salt or solvate thereof (e.g. a compound of Formula (Ia)). In some embodiments, the combination comprises about 5 mg/kg, about 10 mg/kg, about 15 mg/kg, about 20 mg/kg, or about 25 mg/kg per body weight of a compound disclosed herein.

In some embodiments, the combination comprises a PD-1 inhibitor. PD-1 inhibitors useful in the combinations described herein include any molecule capable of inhibiting, blocking, abrogating or interfering with the activity or expression of PD-1. In some embodiments, a PD-1 inhibitor can be a small molecule compound, a nucleic acid, a polypeptide, an antibody, a peptibody, a diabody, a minibody, a single-chain variable fragment (ScFv), or a functional fragment or variant thereof. In some embodiments, the PD-1 inhibitor is a small molecule compound (e.g., a compound having a molecule weight of less than about 1000 Da.). In some instances, useful PD-1 inhibitors in the combinations described herein include nucleic acids and polypeptides. In some embodiments, the PD-1 inhibitor is a polypeptide (e.g., macrocyclic polypeptide). In some embodiments, the PD-1 inhibitor is an antibody, peptibody, diabody, minibody, ScFv, or a functional fragment thereof.

In some embodiments, the PD-1 inhibitor is AMP-224 (GSK). AMP-224 is a recombinant fusion protein comprising an extracellular domain of the PD-1 ligand programmed cell death ligand 2 (PD-L2) and an Fc region of human IgG. Certain cancers can evade and suppress the immune system, in part, and without being bound by any theory, by interactions between PD-1 and B7-H1. AMP-224 blocks this interaction and therefore appears to overcome immune suppression.

In some embodiments, the PD-1 inhibitor is a PD-1 antibody. In some embodiments, the PD-1 antibody is a monoclonal or polyclonal antibody. In certain embodiments, the PD-1 antibody is a monoclonal antibody.

PD-1 antibodies include all known types of antibodies and functional fragments thereof, including but not limited to, those exemplified herein such as, for example, human antibodies, mouse antibodies, chimeric antibodies, humanized antibodies, or chimeric humanized antibodies.

In some embodiments, the PD-1 antibody is a human antibody. In another embodiment, the PD-1 antibody is a mouse antibody. In some embodiment, the PD-1 antibody is a chimeric antibody. In some embodiment, the PD-1 antibody is a humanized antibody. In some embodiment, the PD-1 antibody is a chimeric humanized antibody. The PD-1 antibody is a human antibody or humanized antibody. In some embodiments, the PD-1 antibody is nivolumab, pembrolizumab, pidilizumab, EGN2810, PDR 001, or MEDI0680. In some embodiments, two or more PD-1 antibodies are administered in combination with a compound of Formula (I) as described herein.

In some embodiments, the PD-1 antibody is nivolumab. Nivolumab (marketed as OPDIVO®, Registered Trademark) is a fully human monoclonal antibody directed against PD-1 with immunopotentiation activity. Without being bound by theory, nivolumab binds to and blocks the activation of PD-1 by its cognate ligands, resulting in the activation of T-cells and cell-mediated immune responses against tumor cells or pathogens.

In some embodiments, the PD-1 antibody is pembrolizumab. Pembrolizumab (MK-3475, marketed as KEYTRUDA®, Registered Trademark) is a humanized monoclonal IgG4 antibody directed against human cell surface receptor PD-1 with potential immuno-potentiating activity. Without being bound by theory, pembrolizumab binds to PD-1, an inhibitory signaling receptor expressed on the surface of activated T cells and blocks the binding to and activation of PD-1 by its cognate ligands. The blocking of binding and activity results in the activation of T-cell-mediated immune responses against tumor cells.

In some embodiments, the PD-1 antibody is pidilizumab. Pidilizumab (CT-011) is a humanized monoclonal antibody directed against human PD-1 with immunomodulating and antitumor activities. Without being bound by theory, pidilizumab blocks interaction between the receptor PD-1 with its ligands, resulting in the attenuation of apoptotic processes in lymphocytes, primarily effector/memory T cells, and the augmentation of the anti-tumor activities of NK cells.

In some embodiments, the PD-1 antibody is REGN2810 (also known as cemiplimab). REGN2810 is a human monoclonal antibody directed against PD-1, with potential immune checkpoint inhibitory and antineoplastic activity. Without being bound by theory REGN2810 binds to PD-1, inhibits binding to its cognate ligand, and prevents the activation of its downstream signaling pathways. This restores immune function through the activation of cytotoxic T-cells.

In some embodiments, the PD-1 antibody is PDR 001 (also known as spartalizumab). PDR 001 is a fully humanized monoclonal antibody directed against PD-1, with immune checkpoint inhibitory and antineoplastic activities. Without being bound by theory, PDR 001 binds to PD-1 expressed on activated T-cells and blocks the interaction with its cognate ligands. The inhibition of ligand binding prevents PD-1-mediated signaling and results in both T-cell activation and the induction of T-cell-mediated immune responses against tumor cells.

In some embodiments, the PD-1 antibody is MEDI0680 (also known as durvalumab and marketed as IMFINZI®, Registered Trademark. MEDI0680 is a monoclonal antibody directed against the PD-1, with potential immunomodulating and anti-neoplastic activity. Without being bound by theory, MEDI0680 inhibits the activation of PD-1 and its downstream signaling pathways. This inhibition restores immune function through the activation both of T-cells and cell-mediated immune responses against PD-1 overexpressing tumor cells.

In some embodiments, the PD-1 antibody is of any antibody isotype. The term isotype refers to the antibody class that is encoded by heavy chain constant region genes. The heavy chains of a given antibody or functional fragment determine the class of that antibody or functional fragment: IgM, IgG, IgA, IgD or IgE. Each class can have either κ or λ light chains. The term subclass refers to the minor differences in amino acid sequences of the heavy chains that differentiate the subclasses. In humans there are two subclasses of IgA (subclasses IgA1 and IgA2) and there are four subclasses of IgG (subclasses IgG1, IgG2, IgG3 and IgG4). Such classes and subclasses are well known in the art.

Useful PD-1 antibodies bind to PD-1 with sufficient strength to inhibit activity of PD-1. The term "bind" as used herein refer to an interaction between molecules to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions or forces. Binding of an antibody or functional fragment thereof can be detected using, for example, an enzyme-linked immunosorbent assay or any one of a number of methods that are well known in the art.

The PD-1 antibody can be present in an amount as a measure with regards to the weight of the patient in need thereof. For example, the PD-1 antibody can be present in an amount from about 0.1 mg/kg to about 30 mg/kg, from about 0.1 mg/kg to about 25 mg/kg, from about 0.1 mg/kg to about 20 mg/kg, from about 0.1 mg/kg to about 15 mg/kg, from about 0.1 mg/kg to about 10 mg/kg, from about 0.1 mg/kg to about 7.5 mg/kg, from about 0.1 mg/kg to about 5 mg/kg, from about 0.1 mg/kg to about 2.5 mg/kg, or from about 0.1 mg/kg to about 1 mg/kg. In some embodiments, the PD-1 antibody is present in an amount of about 0.5 mg/kg to about 30 mg/kg, about 0.5 mg/kg to about 25 mg/kg, about 0.5 mg/kg to about 20 mg/kg, about 0.5 mg/kg to about 15 mg/kg, about 0.5 mg/kg to about 10 mg/kg, about 0.5 mg/kg to about 7.5 mg/kg, about 0.5 mg/kg to about 5 mg/kg, about 0.5 mg/kg to about 2.5 mg/kg, or about 0.5 mg/kg to about 1 mg/kg. In some embodiments, the PD-1 antibody is present in an amount of about 0.5 mg/kg to about 5 mg/kg or about 0.1 mg/kg to about 10 mg/kg. In some embodiments, the PD-1 antibody is present in an amount of about 0.5 mg/kg to about 15 mg/kg or about 0.1 mg/kg to about 20 mg/kg.

In the PD-1 antibody is present at an amount of about 0.1 mg/kg, 0.5 mg/kg, 1 mg/kg, 2 mg/kg, 3 mg/kg, 4 mg/kg, 5 mg/kg, 10 mg/kg, 15 mg/kg, 20 mg/kg, or 30 mg/kg. In some embodiments, the PD-1 antibody is present at an amount of about: 1 mg/kg, 2 mg/kg, 3 mg/kg, or 5 mg/kg.

In some embodiments, the PD-1 antibody is present in the combination at an amount of about 1 mg, 5 mg, 10 mg, 15 mg, 20 mg, 25 mg, 30 mg, 40 mg, 50 mg, 60 mg, 70 mg, 75 mg, 80 mg, 90 mg, 100 mg, 150 mg, 200 mg, 250 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg. In some embodiments, the PD-1 antibody is present in the combination at an amount of about 1 mg to about 10 mg, about 10 mg to about 20 mg, about 25 mg to about 50 mg, about 30 mg to about 60 mg, about 40 mg to about 50 mg, about 50 mg to about 100 mg, about 75 mg to about 150 mg, about 100 mg to about 200 mg, about 200 mg to about 500 mg, about 500 mg to about 1000 mg, about 1000 mg to about 1200 mg, about 1000 mg to about 1500 mg, about 1200 mg to about 1500 mg, or about 1500 mg to about 2000 mg.

In some embodiments, the PD-1 antibody is present in the combination in an amount of about 0.1 mg/mL, 0.5 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, 100 mg/mL, 150 mg/mL, 200 mg/mL, 250 mg/mL, 300 mg/mL, 400 mg/mL, or 500 mg/mL. In some embodiments, the PD-1 antibody is present in the combination in an amount of about 1 mg/mL to about 10 mg/mL, about 5 mg/mL to about 10 mg/mL, about 5 mg/mL to about 15 mg/mL, about 10 mg/mL to about 25 mg/mL; about 20 mg/mL to about 30 mg/mL; about 25 mg/mL to about 50 mg/mL, or about 50 mg/mL to about 100 mg/mL.

In certain embodiments, the therapeutically effective amount of a PD-1 antibody is determined as an amount provided in a package insert provided with the PD-1 antibody. The term "package insert" refers to instructions customarily included in commercial packages of pharmaceuticals approved by the FDA or a similar regulatory agency of a country other than the USA, which contains information about, for example, the usage, dosage, administration, contraindications, and/or warnings concerning the use of such medicaments.

In some embodiments, the compound as described herein can be provided in amounts that are synergistic with the amount of the PD-1 inhibitor. The term synergistic refers to a combination described herein (e.g., a compound of Formula (Ia) and a PD-1 inhibitor, including co-administration with another active agent such as an anti-cancer agent described herein) or a combination of regimens that is more effective than the additive effects of each individual therapy or regimen.

A synergistic effect of a combination described herein can permit the use of lower dosages of one or more of the components of the combination (e.g., a compound of Formula (Ia) and a PD-1 inhibitor). A synergistic effect can permit less frequent administration of at least one of the administered therapies (e.g., a compound of Formula (Ia) or a PD-1 inhibitor) to a subject with a disease, disorder, or condition described herein. Such lower dosages and reduced frequency of administration can reduce the toxicity associated with the administration of at least one of the therapies to a subject without reducing the efficacy of the treatment. A synergistic effect avoids or reduces adverse unwanted side effects associated with the use of any therapy.

Further Forms of Compounds

In some embodiments, a compound disclosed herein possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by forming diastereomeric salts and separation by recrystallization, or chromatography, or any combination thereof. Jean Jacques, Andre Collet, Samuel H. Wilen, "Enantiomers, Racemates and Resolutions," John Wiley and Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design of prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews*, 56:53-102, 2004; Aesop Cho, "Recent Advances in Oral Prodrug Discovery," *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

In some embodiments, some of the compounds described herein may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g., with a radioisotope) or by another means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine, chlorine, and iodine such as, for example, $^2H$, $^3H$, $^{13}C$, $^{14}C$, $^{15}N$, $^{18}O$, $^{17}O$, $^{35}S$, $^{18}F$, $^{36}Cl$, and $^{125}I$. In one aspect, isotopically labeled compounds described herein, for example those into which radioactive isotopes such as $^3H$ and $^4C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound disclosed herein with acids. Pharmaceutically acceptable salts are also obtained by reacting a compound disclosed herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g., lithium, sodium, potassium), an alkaline earth ion (e.g., magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

A pharmaceutically acceptable salt includes the solvent addition forms, particularly solvates. Solvates contain either stoichiometric or non-stoichiometric amounts of a solvent and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Pharmaceutical Compositions

In one aspect, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound disclosed herein with other chemical components (i.e., pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds disclosed herein are administered orally.

In some embodiments, the pharmaceutical formulation is in the form of a tablet. In other embodiments, pharmaceutical formulations of the compounds disclosed herein are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound disclosed herein is formulated for use as an aerosol, a mist or a powder.

For buccal or sublingual administration, the compositions may take the form of tablets, lozenges, or gels formulated in a conventional manner.

In some embodiments, compounds disclosed herein are prepared as transdermal dosage forms.

In one aspect, a compound disclosed herein is formulated into a pharmaceutical composition suitable for intramuscular, subcutaneous, or intravenous injection.

In some embodiments, the compound disclosed herein is be administered topically and can be formulated into a variety of topically administrable compositions, such as solutions, suspensions, lotions, gels, pastes, medicated sticks, balms, creams or ointments.

In some embodiments, the compounds disclosed herein are formulated in rectal compositions such as enemas, rectal gels, rectal foams, rectal aerosols, suppositories, jelly suppositories, or retention enemas.

Pharmaceutical compositions and dosage forms described herein typically include one or more excipients. Suitable excipients are well known to those skilled in the art of pharmacy. Whether a certain excipient is suitable for incorporation into a pharmaceutical composition or dosage form depends on a variety of factors such as, for example, the intended route of administration to the patient. Pharmaceutical compositions described herein can include other agents such as stabilizers, lubricants, buffers, and disintegrants that can reduce the rate by which an active ingredient can decompose in a certain formulation.

Pharmaceutical compositions described herein can in certain instances include additional active agents other than those in the combinations described herein (e.g., an anti-cancer agent such as those described herein) in an amount provided herein.

In some embodiments, the compounds disclosed herein are provided in an oral dosage form such as a tablet or capsule. In some embodiment, the compounds disclosed herein are supplied as a powder (e.g., lyophilized powder) that can be resuspended in a liquid suitable for parenteral administration.

PD-1 inhibitors described herein can be provided in forms convenient to or facilitate their administration to a patient. For example, where the PD-1 inhibitor is a PD-1 antibody as described herein, the PD-1 inhibitor can be formulated as a ready to use solution for parenteral administration. In other examples, the PD-1 inhibitor, including for example a PD-1 antibody, can be formulated as a powder (e.g., lyophilized powder) that can be resuspended in a liquid suitable for parenteral administration. In one embodiment, the combination includes a PD-1 antibody formulated for intravenous administration. In still another embodiment the combination includes a compound of formula I formulated as an oral dosage form (e.g., a tablet or capsule) and a PD-1 inhibitor formulated for intravenous administration.

Combinations described herein can be provided as controlled release pharmaceutical products, which have a goal of improving drug therapy over that achieved by their non-controlled counterparts. Controlled release formulations can extend activity of the drug, reduce dosage frequency, and increase subject compliance. In addition, controlled release formulations can be used to affect the time of onset of action or other characteristics, such as blood levels of the drug, and can thus affect the occurrence of side (e.g., adverse) effects.

Methods of Treatment

The combinations and pharmaceutical compositions described herein are useful for treating diseases, disorders, or alleviating or eliminating the symptoms of diseases and disorders such as, for example, cancer.

In an aspect, described herein is a method of treating cancer in a patient in need thereof, the method comprising administering to the patient a combination comprising a SHP2 inhibitor compound as described herein, or a pharmaceutically acceptable salt or solvate thereof (e.g. a compound of Formula (Ia)), and a PD-1 inhibitor.

In some embodiments, the cancer is in the form of a tumor. In some embodiments, the cancer is selected from squamous cell carcinoma, non-squamous cell carcinoma, non-small cell lung cancer (NSCLC), small cell lung cancer, melanoma, hepatocellular carcinoma, renal cell carcinoma, ovarian cancer, head and neck cancer, urothelial cancer, breast cancer, prostate cancer, glioblastoma, colorectal cancer, pancreatic cancer, lymphoma, leiomyosarcoma, liposarcoma, synovial sarcoma, or malignant peripheral sheath tumor (MPNST). In some embodiments, the cancer is squamous cell carcinoma. In some embodiments, the cancer is non-squamous cell carcinoma. In some embodiments, the cancer is non-small cell lung cancer (NSCLC). In some embodiments, the cancer is small cell lung cancer. In some embodiments, the cancer is melanoma. In some embodiments, the cancer is hepatocellular carcinoma. In some embodiments, the cancer is renal cell carcinoma. In some embodiments, the cancer is ovarian cancer. In some embodiments, the caner is head and neck cancer. In some embodiments, the cancer is urothelial cancer. In some embodiments, the cancer is breast cancer (e.g., HER2 negative or HER2 positive breast cancer). In some embodiments, the cancer is prostate cancer. In some embodiments, the cancer is glioblastoma. In some embodiments, the cancer is colorectal cancer. In some embodiments, the care is pancreatic cancer. In some embodiments, the cancer is lymphoma. In some embodiments, the cancer is synovial sarcoma. In some embodiments, the cancer is malignant peripheral sheath tumor (MPNST).

In some embodiments, the tumor is a solid tumor. In some embodiments, the method of treating cancer reduces the tumor volume or tumor burden in the patient. In some embodiments, the tumor is reduced in volume from 5% to 95% or 5% to 50% or any value therein. In some embodiments, the tumor is reduced in volume by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the tumor is reduced in volume by at least 5%, at least 10%, at least 20%, at least 30%, at least 40%, or at least 50%. In some embodiments, the tumor is reduced by about 10% to about 99%. In some embodiments, the tumor is reduced by about 10% to about 20%, about 10% to about 30%, about 10% to about 40%, about 10% to about 50%, about 10% to about 60%, about 10% to about 70%, about 10% to about 80%, about 10% to about 90%, about 10% to about 99%, about 20% to about 30%, about 20% to about 40%, about 20% to about 50%, about 20% to about 60%, about 20% to about 70%, about 20% to about 80%, about 20% to about 90%, about 20% to about 99%, about 30% to about 40%, about 30% to about 50%, about 30% to about 60%, about 30% to about 70%, about 30% to about 80%, about 30% to about 90%, about 30% to about 99%, about 40% to about 50%, about 40% to about 60%, about 40% to about 70%, about 40% to about 80%, about 40% to about 90%, about 40% to about 99%, about 50% to about 60%, about 50% to about 70%, about 50% to about 80%, about 50% to about 90%, about 50% to about 99%, about 60% to about 70%, about 60% to about 80%, about 60% to about 90%, about 60% to about 99%, about 70% to about 80%, about 70% to about 90%, about 70% to about 99%, about 80% to about 90%, about 80% to about 99%, or about 90% to about 99%. In some embodiments, the tumor is reduced by about 10%, about 20%, about 30%, about 40%, about 50%, about 60%, about 70%, about 80%, about 90%, or about 99%. In some embodiments, the tumor is reduced by at least about 10%, about 20%, about 30%, about 40%, about 50%, about 60%, about 70%, about 80%, or about 90%. In some embodiments, the tumor is reduced by at most about 20%, about 30%, about 40%, about 50%, about 60%, about 70%, about 80%, about 90%, or about 99%.

In some embodiments, the method of treating cancer results in reduced tumor growth over the treatment regime. In some embodiments, the treatment regime is about 1 week to about 12 weeks. In some embodiments, the treatment regime is about 1 week to about 2 weeks, about 1 week to about 3 weeks, about 1 week to about 4 weeks, about 1 week to about 5 weeks, about 1 week to about 6 weeks, about 1 week to about 7 weeks, about 1 week to about 8 weeks, about 1 week to about 9 weeks, about 1 week to about 10 weeks, about 1 week to about 11 weeks, about 1 week to about 12 weeks, about 2 weeks to about 3 weeks, about 2 weeks to about 4 weeks, about 2 weeks to about 5 weeks, about 2 weeks to about 6 weeks, about 2 weeks to about 7 weeks, about 2 weeks to about 8 weeks, about 2 weeks to about 9 weeks, about 2 weeks to about 10 weeks, about 2 weeks to about 11 weeks, about 2 weeks to about 12 weeks, about 3 weeks to about 4 weeks, about 3 weeks to about 5 weeks, about 3 weeks to about 6 weeks, about 3 weeks to about 7 weeks, about 3 weeks to about 8 weeks, about 3 weeks to about 9 weeks, about 3 weeks to about 10 weeks, about 3 weeks to about 11 weeks, about 3 weeks to about 12 weeks, about 4 weeks to about 5 weeks, about 4 weeks to about 6 weeks, about 4 weeks to about 7 weeks, about 4 weeks to about 8 weeks, about 4 weeks to about 9 weeks, about 4 weeks to about 10 weeks, about 4 weeks to about 11 weeks, about 4 weeks to about 12 weeks, about 5 weeks to about 6 weeks, about 5 weeks to about 7 weeks, about 5 weeks to about 8 weeks, about 5 weeks to about 9 weeks, about 5 weeks to about 10 weeks, about 5 weeks to about 11 weeks, about 5 weeks to about 12 weeks, about 6 weeks to about 7 weeks, about 6 weeks to about 8 weeks, about 6 weeks to about 9 weeks, about 6 weeks to about 10 weeks, about 6 weeks to about 11 weeks, about 6 weeks to about 12 weeks, about 7 weeks to about 8 weeks, about 7 weeks to about 9 weeks, about 7 weeks to about 10 weeks, about 7 weeks to about 11 weeks, about 7 weeks to about 12 weeks, about 8 weeks to about 9 weeks, about 8 weeks to about 10 weeks, about 8 weeks to about 11 weeks, about 8 weeks to about 12 weeks, about 9 weeks to about 10 weeks, about 9 weeks to about 11 weeks, about 9 weeks to about 12 weeks, about 10 weeks to about 11 weeks, about 10 weeks to about 12 weeks, or about 11 weeks to about 12 weeks. In some embodiments, the treatment regime is about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In some embodiments, the treatment regime is at least about 1 week, about 2 weeks, about 3 weeks, about 4 weeks, about 5 weeks, about 6 weeks, about 7 weeks, about 8 weeks, about 9 weeks, about 10 weeks, or about 11 weeks. In some embodiments, the treatment regime is at most about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In some embodiments, the tumor grows about 50% over the duration of the treatment regime to about 600% over the duration of the treatment regime. In some embodiments, the tumor grows about 50% over the duration of the treatment regime to about 100% over the duration of the treatment regime, about 50% over the duration of the treatment regime to about 150% over the duration of the treatment regime, about 50% over the duration of the treatment regime to about 200% over the duration of the treatment regime, about 50% over the duration of the treatment regime to about 250% over the duration of the treatment regime, about 50% over the duration of the treatment regime to about 300% over the duration of the treatment regime, about 50% over the duration of the treatment regime to about 350% over the duration of the treatment regime, about 50% over the duration of the treatment regime to about 400% over the duration of the treatment regime, about 50% over the duration of the treatment regime to about 450% over the duration of the treatment regime, about 50% over the duration of the treatment regime to about 500% over the duration of the treatment regime, about 50% over the duration of the treatment regime to about 550% over the duration of the treatment regime, about 50% over the duration of the treatment regime to about 600% over the duration of the treatment regime, about 100% over the duration of the treatment regime to about 150% over the duration of the treatment regime, about 100% over the duration of the treatment regime to about 200% over the duration of the treatment regime, about 100% over the duration of the treatment regime to about 250% over the duration of the treatment regime, about 100% over the duration of the treatment regime to about 300% over the duration of the treatment regime, about 100% over the duration of the treatment regime to about 350% over the duration of the treatment regime, about 100% over the duration of the treatment regime to about 400% over the duration of the treatment regime, about 100% over the duration of the treatment regime to about 450% over the duration of the treatment regime, about 100% over the duration of the treatment regime to about 500% over the duration of the treatment regime, about 100% over the duration of the treatment regime to about 550% over the duration of the treatment regime, about 100% over the duration of the treatment regime to about 600% over the duration of the treatment regime, about 150% over the duration of the treatment regime to about 200% over the duration of the treatment regime, about 150% over the duration of the treatment regime to about 250% over the duration of the treatment regime, about 150% over the duration of the treatment regime to about 300% over the duration of the treatment regime, about 150% over the duration of the treatment regime to about 350% over the duration of the treatment regime, about 150% over the duration of the treatment regime to about 400% over the duration of the treatment regime, about 150% over the duration of the treatment regime to about 450% over the duration of the treatment regime, about 150% over the duration of the treatment regime to about 500% over the duration of the treatment regime, about 150% over the duration of the treatment regime to about 550% over the duration of the treatment regime, about 150% over the duration of the treatment regime to about 600% over the duration of the treatment regime, about 200% over the duration of the treatment regime to about 250% over the duration of the treatment regime, about 200% over the duration of the treatment regime to about 300% over the duration of the treatment regime, about 200% over the duration of the treatment regime to about 350% over the duration of the treatment regime, about 200% over the duration of the treatment regime to about 400% over the duration of the treatment regime, about 200% over the duration of the treatment regime to about 450% over the duration of the treatment regime, about 200% over the duration of the treatment regime to about 500% over the duration of the treatment regime, about 200% over the duration of the treatment regime to about 550% over the duration of the treatment regime, about 200% over the duration of the treatment regime to about 600% over the duration of the treatment regime, about 250% over the duration of the treatment regime to about 300% over the duration of the treatment regime, about 250% over the duration of the treatment regime to about 350% over the duration of the treatment regime, about 250% over the duration of the treatment regime to about 400% over the duration of the treatment regime, about 250% over the duration of the treatment regime to about 450% over the duration of the treatment regime, about 250% over the duration of the treatment regime to about 500% over the duration of the treatment regime, about 250% over the duration of the treatment regime to about 550% over the duration of the treatment regime, about 250% over the duration of the treatment regime to about 600% over the duration of the treatment regime, about 300% over the duration of the treatment regime to about 350% over the duration of the treatment regime, about 300% over the duration of the treatment regime to about 400% over the duration of the treatment regime, about 300% over the duration of the treatment regime to about 450% over the duration of the treatment regime, about 300% over the duration of the treatment regime to about 500% over the duration of the treatment regime, about 300% over the duration of the treatment regime to about 550% over the duration of the treatment regime, about 300% over the duration of the treatment regime to about 600% over the duration of the treatment regime, about 350% over the duration of the treatment regime to about 400% over the duration of the treatment regime, about 350% over the duration of the treatment regime to about 450% over the duration of the treatment regime, about 350% over the duration of the treatment regime to about 500% over the duration of the treatment regime, about 350% over the duration of the treatment regime to about 550% over the duration of the treatment regime, about 350% over the duration of the treatment regime to about 600% over the duration of the treatment regime, about 400% over the duration of the treatment regime to about 450% over the duration of the treatment regime, about 400% over the duration of the treatment regime to about 500% over the duration of the treatment regime, about 400% over the duration of the treatment regime to about 550% over the duration of the treatment regime, about 400% over the duration of the treatment regime to about 600% over the duration of the treatment regime, about 450% over the duration of the treatment regime to about 500% over the duration of the treatment regime, about 450% over the duration of the treatment regime to about 550% over the duration of the treatment regime, about 450% over the duration of the treatment regime to about 600% over the duration of the treatment regime, about 500% over the duration of the treatment regime to about 550% over the duration of the treatment regime, about 500% over the duration of the treatment regime to about 600% over the duration of the treatment regime, or about 550% over the duration of the treatment regime to about 600% over the duration of the treatment regime. In some embodiments, the tumor grows about 50% over the duration of the treatment regime, about 100% over the duration of the treatment regime, about 150% over the duration of the treatment regime, about 200% over the duration of the treatment regime, about 250% over the duration of the treatment regime, about 300% over the duration of the treatment regime, about 350% over the duration of the treatment regime, about 400% over the duration of the treatment regime, about 450% over the duration of the treatment regime, about 500% over the duration of the treatment regime, about 550% over the duration of the treatment regime, or about 600% over the duration of the treatment regime. In some embodiments, the tumor grows at least about 50% over the duration of the treatment regime, about 100% over the duration of the treatment regime, about 150% over the duration of the treatment regime, about 200% over the duration of the treatment regime, about 250% over the duration of the treatment regime, about 300% over the duration of the treatment regime, about 350% over the duration of the treatment regime, about 400% over the duration of the treatment regime, about 450% over the duration of the treatment regime, about 500% over the duration of the treatment regime, or about 550% over the duration of the treatment regime. In some embodiments, the tumor grows at most about 100% over the duration of the treatment regime, about 150% over the duration of the treatment regime, about 200% over the duration of the treatment regime, about 250% over the duration of the treatment regime, about 300% over the duration of the treatment regime, about 350% over the duration of the treatment regime, about 400% over the duration of the treatment regime, about 450% over the duration of the treatment regime, about 500% over the duration of the treatment regime, about 550% over the duration of the treatment regime, or about 600% over the duration of the treatment regime.

In some embodiments, the cancer is a hematological cancer. In some embodiments, the cancer is a hematological cancer selected from lymphoma, Non-Hodgkin's lymphoma (NHL), Hodgkin's Lymphoma, Reed-Sternberg disease, multiple myeloma (MM), acute myelogenous leukemia (AML), chronic myelogenous leukemia (CML), acute lymphocytic leukemia (ALL), or chronic lymphocytic leukemia (CLL). In some embodiments, the cancer is Hodgkin's Lymphoma or Reed-Sternberg disease.

In some embodiments, the cancer is lymphoma. In some embodiments, the cancer is Non-Hodgkin lymphoma (NHL). In some embodiments, the NHL is indolent NHL (e.g., follicular lymphoma (FL); lymphoplasmacytic lymphoma (LL); marginal zone lymphoma (MZL) or primary cutaneous anaplastic large cell lymphoma) or aggressive NHL (e.g., Diffuse large B-cell lymphoma (DLBCL); Follicular large cell lymphoma stage III; anaplastic large cell lymphoma; extranodal NK-/T-cell lymphoma; lymphomatoid granulmatosis; angioimmunoblastic T-cell lymphoma; peripheral T-cell lymphoma; intravascular large B-cell lymphoma; Burkitt lymphoma; lymphoblastic lymphoma; adult T-cell leukemia/lymphoma; or mantle cell lymphoma). In some embodiments, the cancer is Hodgkin's lymphoma (e.g., classical or nodular lymphocyte-predominant). In some embodiments, the Hodgkin's Lymphoma includes Reed-Sternberg cells and can cause Reed-Sternberg disease. In some embodiments, the cancer is multiple myeloma (MM). In some embodiments, the cancer is acute myelogenous leukemia (AML). In some embodiments, the cancer is chronic myelogenous leukemia (CML). In some embodiments, the cancer is chronic lymphocytic leukemia (CLL), (e.g., Binet Stage A cancer or a Binet Stage B cancer). In some embodiments, the cancer is acute lymphocytic leukemia (ALL), (e.g., T-cell or B-cell lymphoblastic leukemia).

In some embodiments, the cancer is a Stage I, Stage II, Stage, III, or Stage IV cancer. In some embodiments, the cancer is a Stage I cancer (e.g., Stage IA, IB, or IC). In some embodiments, the cancer is a Stage II cancer (e.g., Stage IIA or IIB). In some embodiments, the cancer is a Stage III cancer, (e.g., Stage IIIA, IIIB, or IIIC). In some embodiments, the cancer is a Stage IV cancer, (e.g., Stage IVA or IVB).

The combinations described herein can be administered to a cancer patient at any time following diagnosis. For example, the cancer patient can be treatment naive (i.e., has not received a cancer therapy for the diagnosed cancer). The cancer patient can be treatment naive for one cancer but can be diagnosed with one or more other cancers resulting from, for example, metastasis or malignancy. The cancer patient can be immune checkpoint naive for one or more cancers. The cancer patient can have a cancer that is refractory. In certain instances, the combinations described herein are administered as a first line therapy (e.g., the first therapy administered to a treatment naive cancer patient) to a patient in need thereof.

In some embodiments, the method of treating cancer inhibits metastasis of the cancer in the patient. In some embodiments, metastasis is inhibited by at least about 5%, 10%, 20%, 30%, 40%, 50%, 60%, 70%, 80%, 90%, or 100%.

In some embodiments, the method of treating cancer reduces pre-existing tumor metastasis in the patient. In some embodiments, preexisting tumor metastasis is reduced by at least about 5%, 10%, 20%, 30%, 40%, 50%, 60%, 70%, 80%, 90%, or 100%.

In some embodiments, the method of treating cancer prolongs or increases the time to disease progression of the cancer in the patient (including progression between advanced stages; e.g., progression from Stage III to Stage IV cancer). In some embodiments, the increase is a comparison between the time to disease progression with and without treatment. In some embodiments, the methods described herein prolong the time to disease progression by at least 1 week, 2 weeks, 3 weeks, 4 weeks, 1 month, 2 months, 3 months, 4 months, 5 months, 6 months, 7 months, 8 months, 9 months, 10 months, 11 months, 1 year, or more, including values therein.

In some embodiments, the method of treating cancer prolongs the survival of the patient. In some embodiments, the method of treating cancer increases progression-free survival of the patient. In some embodiments, the method of treating cancer prolongs the time to disease progression of the cancer in the patient. In some embodiments, the method of treating cancer prolongs the survival of the patient. In some embodiments, the method of treating cancer increases progression-free survival of the patient. In some embodiments, survival is prolonged by at least 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, or more, including values therein.

In some embodiments, the patient is treatment naïve patient is treatment naïve.

In some embodiments, the method comprises administering the combinations described herein to the patient as a first line therapy. In some embodiments, the method comprises administering the combination described herein to the patient as a second, third, fourth, fifth, or sixth line of treatment. In some embodiments, the method comprises administering the combination described herein as a second line of treatment. In some embodiments, the method comprises administering the combination described herein as a third line of treatment.

In some embodiments, the method comprises administering the combinations described herein to the patient following treatment with at least one anti-cancer therapy. In some embodiments, the anti-cancer therapy is chemotherapy, radiotherapy, surgery, targeted therapy, immunotherapy, or a combination thereof. In some embodiments, the anti-cancer therapy is chemotherapy. In some embodiments, the anti-cancer therapy is radiotherapy. In some embodiments, the anti-cancer therapy is cancer surgery. In some embodiments, the anti-cancer therapy is tumor resection or excision. In some embodiments, the anti-cancer therapy is immunotherapy.

In some embodiments, the method comprises administering the combination described herein to a patient who has failed at least one PD-1 therapy.

In some embodiments, the cancer is resistant to at least one anti-cancer agent.

Methods of Dosing and Treatment Regimens

In another aspect, the combination described herein are used in the preparation of medicaments for the treatment of diseases or conditions described herein.

In certain embodiments, the combination disclosed herein are administered for prophylactic and/or therapeutic treatments. In certain therapeutic applications, the combinations are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, the combinations disclosed herein are administered to a patient susceptible to or otherwise at risk of a particular disease, disorder or condition.

In some embodiments, the method comprises administering the combinations described herein to the patient orally or by intraperitoneal methods (i.p.) or a combination thereof. In some embodiments, the combination is administered orally. In some embodiments, the combination is administered orally. In some embodiments, the combination is administered by i.p. methods. In some embodiments, the combination is administered intravenously (I.V.).

Doses employed for adult human treatment are typically in the range of 0.01 mg-5000 mg per day or from about 0.01 mg to about 1000 mg per day. In one embodiment, the desired dose is conveniently presented in a single dose or in divided doses.

In certain embodiments, the dose of drug being administered may be temporarily reduced or temporarily suspended for a certain length of time (i.e., a "drug holiday").

In some embodiments, the method comprises administering the combinations described herein to the patient daily, weekly, or monthly. In some embodiments, the combination is administered daily. In some embodiments, the combination is administered weekly. In some embodiments, the combination is administered bi-weekly. In some embodiments, the combination is administered monthly. In some embodiments, the combination is administered bi-monthly.

The combinations described herein can be administered, for example, once a day (QD), twice daily (BID), once a week (QW), twice weekly (BID), three times a week (TIW), or monthly (QM). In some embodiments, the method comprises administering the combinations described herein QD, BID, or TID. In some embodiments, the combination is administered QD. In some embodiments, the combination is administered BID. In some embodiments, the combination is administered TID. In certain instances, the compound of formula I is administered 2 to 3 times a week. In another embodiment, the compound of formula I is administered QD. The compound can be administered QD for about: 1 day to about 7 days, 1 day to about 14 days, 1 day to about 21 days, 1 day to about 28 days, or daily until disease progression or unacceptable toxicity. The administration of a compound of formula I can, in part, depend upon the tolerance of the patient where greater tolerance can allow greater or more frequent administration.

The term "administered simultaneously", as used herein, is not specifically restricted and means that the compounds of the present disclosure and the additional active agent are substantially administered at the same time, e.g. as a mixture or in immediate subsequent sequence.

The term "administered sequentially", as used herein, is not specifically restricted and means that the compounds of the present disclosure and the additional active agent are not administered at the same time but one after the other, or in groups, with a specific time interval between administrations. The time interval may be the same or different between the respective administrations of the compounds of the present disclosure and the additional active agent and may be selected, for example, from the range of 2 minutes to 96 hours, 1 to 7 days or one, two, or three weeks. Generally, the time interval between the administrations may be in the range of a few minutes to hours, such as in the range of 2 minutes to 72 hours, 30 minutes to 24 hours, or 1 to 12 hours. Further examples include time intervals in the range of 24 to 96 hours, 12 to 36 hours, 8 to 24 hours, and 6 to 12 hours.

In some embodiments, the SHP2 inhibitor of Formula (I), or a pharmaceutically acceptable salt or solvate thereof and the PD-1 inhibitor are administered concurrently or sequentially. In some embodiments, the SHP2 inhibitor compound described herein and the PD-1 inhibitor are administered sequentially. In some embodiments, the SHP2 inhibitor compound described herein, or a pharmaceutically acceptable salt or solvate thereof (e.g., a compound of Formula (Ia)), is administered QD, BID, or TID; and the PD-1 inhibitor is administered QD, BID, or TID.

The combinations described herein can include administration of each therapy (e.g., a compound of Formula (Ia) and a PD-1 inhibitor), where the administration is performed simultaneously or sequentially (in either order). In some embodiments, the SHP2 inhibitor compound described herein and the PD-1 inhibitor are administered simultaneously (e.g., within at least 1 to 5 min of each other). In other embodiments, the compound described herein and the PD-1 inhibitor are administered sequentially (e.g., within at least 10 min, 15 min, 30 min, 1 h, 2 h, 5 h, 10 h, 12 h, 1 day, 2 days, 5 days, 7 days, 14 days, or 21 days of each other).

In some embodiments, the SHP2 inhibitor compound described herein is administered concurrently with a PD-1 inhibitor. In some embodiments, the compound described herein is administered prior to a PD-1 inhibitor. In some embodiments, the compound described herein is administered after a PD-1 inhibitor.

The combinations described herein can be administered in a regimen. The regimen can be structured to provide therapeutically effective amounts of a SHP2 inhibitor compound described herein and a PD-1 inhibitor over a predetermined period of time (e.g., an administration time). The regimen can be structured to limit or prevent side-effects or undesired complications of each of the components of the combination described herein. The regimen can be structured in a manner that results in increased effect for both therapies of the combination (e.g., synergy). Regimens useful for treating cancer can include any number of days of administration which can be repeated as necessary. Administration periods can be broken by a rest period that includes no administration of at least one therapy. For example, a regimen can include administration periods that include 2, 3, 5, 7, 10, 15, 21, 28, or more days. These periods can be repeated. For example, a regimen can include a set number of days as previously described where the regimen is repeated 1, 2, 3, 4, 5, 6, 7, 8, 9, 10, 11, 12, 13, or more times.

Regimens can include a rest period of at least 1, 2, 3, 5, 7, 10, or more days, where at least one therapy is no longer administered to a patient. The rest period can be determined by, for example, monitoring the reaction of the patient to the drug or by measuring the efficacy of the treatment. A rest period can be applicable to a single therapy, such that only one therapy of a combination described herein is discontinued in the rest period but the other therapy(ies) are still administered. Rest periods can be applied to all of the therapies administered to the subject such that the subject receives no therapy for a set period of time during the rest period.

Regimens described herein for the treatment of cancer using the combinations described herein can be continued until disease progression or unacceptable toxicity.

Biomarkers

In another aspect, presented herein is a method of modulating one or more biomarkers over baseline levels prior to treatment in a patient in need thereof, comprising administering to the patient a combination of a SHP2 inhibitor compound described herein, or a pharmaceutically acceptable salt or solvate thereof, (e.g., a compound of Formula (Ia)); and a PD-1 inhibitor.

In some embodiments, the one or more biomarkers includes proinflammatory cytokines or chemokines that are important in inflammation response and immune system regulation. In some embodiments, the one or more biomarkers include but are not limited to INF-7, IL-10, IL-2, IL-4, IL-5, IL-6, IL-10, IL-12p70, KC/GRO (CXCL1), and M1/M2 macrophage expression.

In some embodiments, the one or more biomarkers in increased or decreased over baseline levels prior to treatment. In some embodiments, the one or more biomarkers is increased over baseline levels. In some embodiments, the one or more biomarkers is decreased over baseline levels.

In some embodiments, the one or more biomarkers is increased by at least 5%, at least 10%, at least 15%, at least 20%, at least 25%, at least 30%, at least 40%, at least 50%, at least 100%, or at least 150%. In some embodiments, the one or more biomarkers is increased by at least 1.5 times, 2 times, 3 times, 4 times, 5 times, 10 times, 15 times, 20 times, or 25 times. In some embodiments, the one or more biomarkers is decreased by at least 5%, at least 10%, at least 15%, at least 20%, at least 25%, at least 30%, at least 40%, at least 50%, at least 100%, or at least 150%. In some embodiments, the one or more biomarkers is decreased by at least 1.5 times, 2 times, 3 times, 4 times, 5 times, 10 times, 15 times, 20 times, or 25 times.

In some embodiments, administering the combinations described herein results in a decrease in KC/GRO by at least 5%, at least 10%, at least 15%, at least 20%, at least 25%, at least 30%, at least 40%, at least 50%, at least 100%, or at least 150%. In some embodiments, the one or more biomarkers is decreased by at least 1.5 times, 2 times, 3 times, 4 times, 5 times, 10 times, 15 times, 20 times, or 25 times. In some embodiments, administering the combinations described herein results in a decrease in KC/GRO by about 5% to about 90%. In some embodiments, administering the combinations described herein results in a decrease in KC/GRO by about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 75%, about 5% to about 90%, about 10% to about 15%, about 10% to about 20%, about 10% to about 25%, about 10% to about 30%, about 10% to about 35%, about 10% to about 40%, about 10% to about 45%, about 10% to about 50%, about 10% to about 75%, about 10% to about 90%, about 15% to about 20%, about 15% to about 25%, about 15% to about 30%, about 15% to about 35%, about 15% to about 40%, about 15% to about 45%, about 15% to about 50%, about 15% to about 75%, about 15% to about 90%, about 20% to about 25%, about 20% to about 30%, about 20% to about 35%, about 20% to about 40%, about 20% to about 45%, about 20% to about 50%, about 20% to about 75%, about 20% to about 90%, about 25% to about 30%, about 25% to about 35%, about 25% to about 40%, about 25% to about 45%, about 25% to about 50%, about 25% to about 75%, about 25% to about 90%, about 30% to about 35%, about 30% to about 40%, about 30% to about 45%, about 30% to about 50%, about 30% to about 75%, about 30% to about 90%, about 35% to about 40%, about 35% to about 45%, about 35% to about 50%, about 35% to about 75%, about 35% to about 90%, about 40% to about 45%, about 40% to about 50%, about 40% to about 75%, about 40% to about 90%, about 45% to about 50%, about 45% to about 75%, about 45% to about 90%, about 50% to about 75%, about 50% to about 90%, or about 75% to about 90%. In some embodiments, administering the combinations described herein results in a decrease in KC/GRO by about 5%, about 10%, about 15%, about 20%, about 25%, about 30%, about 35%, about 40%, about 45%, about 50%, about 75%, or about 90%. In some embodiments, administering the combinations described herein results in a decrease in KC/GRO by at least about 5%, about 10%, about 15%, about 20%, about 25%, about 30%, about 35%, about 40%, about 45%, about 50%, or about 75%. In some embodiments, administering the combinations described herein results in a decrease in KC/GRO by at most about 10%, about 15%, about 20%, about 25%, about 30%, about 35%, about 40%, about 45%, about 50%, about 75%, or about 90%.

In some embodiments, administering the combinations described herein results in a decrease in TNG-alpha by at least 5%, at least 10%, at least 15%, at least 20%, at least 25%, at least 30%, at least 40%, at least 50%, at least 100%, or at least 150%. In some embodiments, the one or more biomarkers is decreased by at least 1.5 times, 2 times, 3 times, 4 times, 5 times, 10 times, 15 times, 20 times, or 25 times. In some embodiments, administering the combinations described herein results in a decrease in TNF-alpha by about 5% to about 90%. In some embodiments, administering the combinations described herein results in a decrease in TNF-alpha by about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 75%, about 5% to about 90%, about 10% to about 15%, about 10% to about 20%, about 10% to about 25%, about 10% to about 30%, about 10% to about 35%, about 10% to about 40%, about 10% to about 45%, about 10% to about 50%, about 10% to about 75%, about 10% to about 90%, about 15% to about 20%, about 15% to about 25%, about 15% to about 30%, about 15% to about 35%, about 15% to about 40%, about 15% to about 45%, about 15% to about 50%, about 15% to about 75%, about 15% to about 90%, about 20% to about 25%, about 20% to about 30%, about 20% to about 35%, about 20% to about 40%, about 20% to about 45%, about 20% to about 50%, about 20% to about 75%, about 20% to about 90%, about 25% to about 30%, about 25% to about 35%, about 25% to about 40%, about 25% to about 45%, about 25% to about 50%, about 25% to about 75%, about 25% to about 90%, about 30% to about 35%, about 30% to about 40%, about 30% to about 45%, about 30% to about 50%, about 30% to about 75%, about 30% to about 90%, about 35% to about 40%, about 35% to about 45%, about 35% to about 50%, about 35% to about 75%, about 35% to about 90%, about 40% to about 45%, about 40% to about 50%, about 40% to about 75%, about 40% to about 90%, about 45% to about 50%, about 45% to about 75%, about 45% to about 90%, about 50% to about 75%, about 50% to about 90%, or about 75% to about 90%. In some embodiments, administering the combinations described herein results in a decrease in TNF-alpha by about 5%, about 10%, about 15%, about 20%, about 25%, about 30%, about 35%, about 40%, about 45%, about 50%, about 75%, or about 90%. In some embodiments, administering the combinations described herein results in a decrease in TNF-alpha by at least about 5%, about 10%, about 15%, about 20%, about 25%, about 30%, about 35%, about 40%, about 45%, about 50%, or about 75%. In some embodiments, administering the combinations described herein results in a decrease in TNF-alpha by at most about 10%, about 15%, about 20%, about 25%, about 30%, about 35%, about 40%, about 45%, about 50%, about 75%, or about 90%.

In some embodiments, administering the combinations described herein results in a M1/M2 macrophage ratio in tumors indicative of a suppression of tumor progression. In some embodiments, administering the combinations described herein results in a M1/M2 macrophage ratio of about 0.1 to about 1.2. In some embodiments, administering the combinations described herein results in a M1/M2 macrophage ratio of about 0.1 to about 0.2, about 0.1 to about 0.3, about 0.1 to about 0.4, about 0.1 to about 0.5, about 0.1 to about 0.6, about 0.1 to about 0.7, about 0.1 to about 0.8, about 0.1 to about 0.9, about 0.1 to about 1, about 0.1 to about 1.1, about 0.1 to about 1.2, about 0.2 to about 0.3, about 0.2 to about 0.4, about 0.2 to about 0.5, about 0.2 to about 0.6, about 0.2 to about 0.7, about 0.2 to about 0.8, about 0.2 to about 0.9, about 0.2 to about 1, about 0.2 to about 1.1, about 0.2 to about 1.2, about 0.3 to about 0.4, about 0.3 to about 0.5, about 0.3 to about 0.6, about 0.3 to about 0.7, about 0.3 to about 0.8, about 0.3 to about 0.9, about 0.3 to about 1, about 0.3 to about 1.1, about 0.3 to about 1.2, about 0.4 to about 0.5, about 0.4 to about 0.6, about 0.4 to about 0.7, about 0.4 to about 0.8, about 0.4 to about 0.9, about 0.4 to about 1, about 0.4 to about 1.1, about 0.4 to about 1.2, about 0.5 to about 0.6, about 0.5 to about 0.7, about 0.5 to about 0.8, about 0.5 to about 0.9, about 0.5 to about 1, about 0.5 to about 1.1, about 0.5 to about 1.2, about 0.6 to about 0.7, about 0.6 to about 0.8, about 0.6 to about 0.9, about 0.6 to about 1, about 0.6 to about 1.1, about 0.6 to about 1.2, about 0.7 to about 0.8, about 0.7 to about 0.9, about 0.7 to about 1, about 0.7 to about 1.1, about 0.7 to about 1.2, about 0.8 to about 0.9, about 0.8 to about 1, about 0.8 to about 1.1, about 0.8 to about 1.2, about 0.9 to about 1, about 0.9 to about 1.1, about 0.9 to about 1.2, about 1 to about 1.1, about 1 to about 1.2, or about 1.1 to about 1.2. In some embodiments, administering the combinations described herein results in a M1/M2 macrophage ratio of about 0.1, about 0.2, about 0.3, about 0.4, about 0.5, about 0.6, about 0.7, about 0.8, about 0.9, about 1, about 1.1, or about 1.2. In some embodiments, administering the combinations described herein results in a M1/M2 macrophage ratio of at least about 0.1, about 0.2, about 0.3, about 0.4, about 0.5, about 0.6, about 0.7, about 0.8, about 0.9, about 1, or about 1.1. In some embodiments, administering the combinations described herein results in a M1/M2 macrophage ratio of at most about 0.2, about 0.3, about 0.4, about 0.5, about 0.6, about 0.7, about 0.8, about 0.9, about 1, about 1.1, or about 1.2.

Definitions

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed invention.

The terms below, as used herein, have the following meanings, unless indicated otherwise:

"Oxo" refers to the =O substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. Preferably, the $C_1$-$C_{10}$ alkyl is any one of methyl, ethyl, n-propyl, isopropyl, and tert-butyl. Unless stated otherwise specifically in the specification, an alkyl group may be optionally substituted as described below.

"Alkylene" refers to a straight or branched divalent hydrocarbon chain linking the rest of the molecule to a radical group. In some embodiments, the alkylene is —$CH_2$—, —$CH_2CH_2$—, or —$CH_2CH_2CH_2$—. In some embodiments, the alkylene is —$CH_2$—. In some embodiments, the alkylene is —$CH_2CH_2$—. In some embodiments, the alkylene is —$CH_2CH_2CH_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy. The term "$C_1$-$C_{10}$ alkoxy" alone or in combination means the group $C_1$-$C_{10}$ alkyl-O—, wherein "$C_1$-$C_{10}$ alkyl" means as defined above, which includes, but not limited to, methoxy (—$OCH_3$), ethoxy (—$OCH_2CH_3$), n-propoxy (—$OCH_2CH_2CH_3$), iso-propoxy (—$OCH(CH_3)_2$), n-butoxy (—$OCH_2CH_2CH_2CH_3$), sec-butoxy (—$OCH(CH_3)CH_2CH_3$), iso-butoxy (—$OCH_2CH(CH_3)_2$), tert-butoxy (—$OC(CH_3)_3$), etc.

"Heteroalkyl" refers to an alkyl radical as described above where one or more carbon atoms of the alkyl is replaced with a O, N (i.e., NH, N-alkyl) or S atom. "Heteroalkylene" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —$OCH_2OMe$, —$OCH_2CH_2OMe$, or —$OCH_2CH_2OCH_2CH_2NH_2$. Representative heteroalkylene groups include, but are not limited to —$OCH_2CH_2O$—, —$OCH_2CH_2OCH_2CH_2O$—, or —$OCH_2CH_2OCH_2CH_2OCH_2CH_2O$—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO₂H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

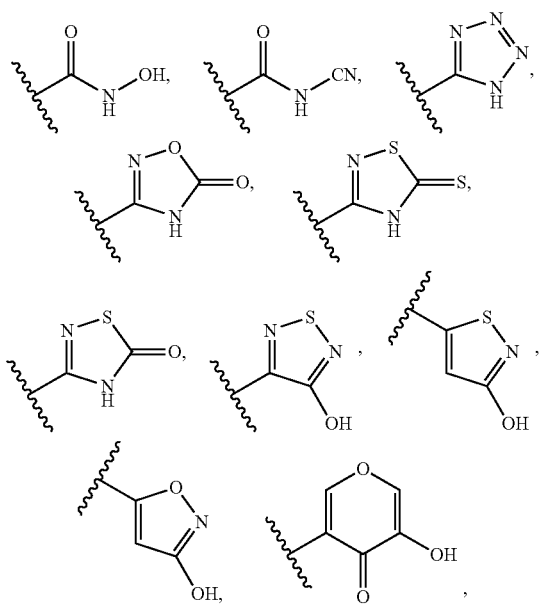

and the like.

"Cycloalkyl" refers to a monocyclic or polycyclic non-aromatic radical, wherein each of the atoms forming the ring (i.e., skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. In some embodiments, a cycloalkyl is a $C_3$-$C_6$cycloalkyl. In some embodiments, the cycloalkyl is monocyclic, bicyclic or polycyclic. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, bicyclo[1.1.1]pentyl, bicyclo[3.3.0]octane, bicyclo[4.3.0]nonane, bicyclo[2.1.1]hexane, bicyclo[2.2.1]heptane, bicyclo[2.2.2]octane, bicyclo[3.2.2]nonane, bicyclo[3.3.2]decane, norbornyl, decalinyl and adamantyl. In some embodiments, the cycloalkyl is monocyclic. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. In some embodiments, the cycloalkyl is bicyclic. Bicyclic cycloalkyl groups include fused bicyclic cycloalkyl groups, spiro bicyclic cycloalkyl groups, and bridged bicyclic cycloalkyl groups. In some embodiments, cycloalkyl groups are selected from among spiro[2.2]pentyl, bicyclo[1.1.1]pentyl, bicyclo[3.3.0]octane, bicyclo[4.3.0]nonane, bicyclo[2.1.1]hexane, bicyclo[2.2.1]heptane, bicyclo[2.2.2]octane, bicyclo[3.2.2]nonane, bicyclo[3.3.2]decane, norbornyl, 3,4-dihydronaphthalen-1(2H)-one and decalinyl. In some embodiments, the cycloalkyl is polycyclic. Polycyclic radicals include, for example, adamantyl, and. In some embodiments, the polycyclic cycloalkyl is adamantyl. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, bicyclic ring (which may include a fused bicyclic heterocycloalkyl (when fused with an aryl or a heteroaryl ring, the heterocycloalkyl is bonded through a non-aromatic ring atom), bridged heterocycloalkyl or spiro heterocycloalkyl), or polycyclic. In some embodiments, the heterocycloalkyl is monocyclic or bicyclic. In some embodiments, the heterocycloalkyl is monocyclic. In some embodiments, the heterocycloalkyl is bicyclic. The nitrogen, carbon or sulfur atoms in the heterocyclyl radical may be optionally oxidized. The nitrogen atom may be optionally quaternized. The heterocycloalkyl radical is partially or fully saturated.

Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). Unless stated otherwise specifically in the specification, a heterocycloalkyl group may be optionally substituted. In some embodiments, the term "3-12 membered heterocyclic group" refers to a saturated or partially unsaturated monocyclic ring containing 3-12, particularly 5-12, more particularly 5-7 carbon atoms and heteroatoms or heteroatom groups or a polycyclic heterocyclic group, the heteroatom or heteroatom group is selected from N, NH, O, C(O), S(O)$_m$ (where m is 0, 1 or 2). In some embodiments, the 3-12, ember heterocyclic groups include aziridinyl, azetidinyl, oxetanyl, pyrrolidinyl, tetrahydrofuranyl, tetrahydrothienyl, piperidinyl, morpholinyl, piperazinyl, thiomorpholine, tetrahydropyranyl, 1,1-dioxothiomorpholinyl, butyrolactamyl, valerolactam, caprolactam, butyrolactone, valerolactone, or caprolactone.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —CO$_2$H, —CO$_2$alkyl, nitro, and amino, including mono- and di-substituted amino groups (e.g., —NH$_2$, —NHR, —NR$_2$), and the protected derivatives thereof. In some embodiments, optional substituents are independently selected from alkyl, alkoxy, haloalkyl, cycloalkyl, halogen, —CN, —NH$_2$, —NH(CH$_3$), —N(CH$_3$)$_2$, —OH, —CO$_2$H, and —CO$_2$alkyl. In some embodiments, optional substituents are independently selected from fluoro, chloro, bromo, iodo, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

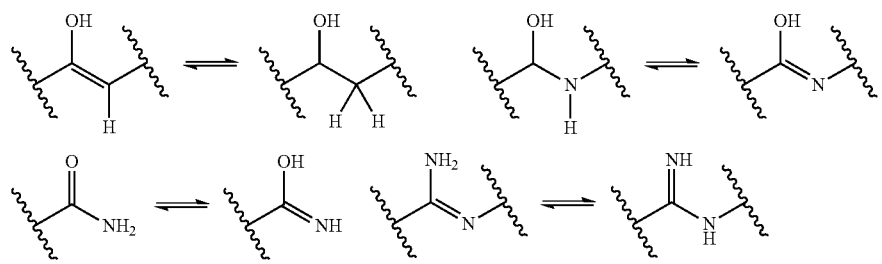

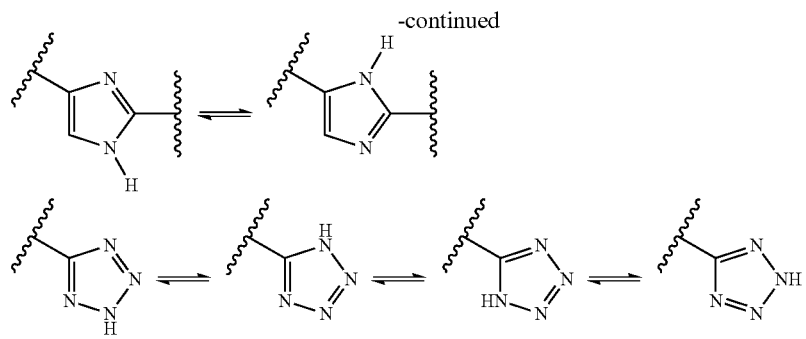

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "pharmaceutical combination" as used herein, means a product that results from the mixing or combining of more than one active ingredient and includes both fixed and non-fixed combinations of the active ingredients. The term "fixed combination" means that the active ingredients, e.g., a compound of Formula (I) and a co-agent, are both administered to a patient simultaneously in the form of a single entity or dosage. The term "non-fixed combination" means that the active ingredients, e.g., a compound of Formula (I) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "cancer" refers to any physiological condition in mammals characterized by unregulated cell growth. Cancers described herein include solid tumors and hematological (blood) cancers. A "hematological cancer" refers to any blood borne cancer and includes, for example, myelomas, lymphomas and leukemias. A "solid tumor" or "tumor" refers to a lesion and neoplastic cell growth and proliferation, whether malignant or benign, and all pre-cancerous and cancerous cells and tissues resulting in abnormal tissue growth. "Neoplastic," as used herein, refers to any form of dysregulated or unregulated cell growth, whether malignant or benign, resulting in abnormal tissue growth.

The term "enhance" refers to an increase or improvement in the function or activity of a protein or cell after administration or contacting with a combination described herein compared to the protein or cell prior to such administration or contact.

The term "anti-cancer agent" is used in accordance with its plain ordinary meaning and refers to a composition having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The term "chemotherapeutic" or "chemotherapeutic agent" is used in accordance with its plain ordinary meaning and refers to a chemical composition or compound having anti-neoplastic properties or the ability to inhibit the growth or proliferation of cells. "Chemotherapy" refers to a therapy or regimen that includes administration of a chemotherapeutic or anti-cancer agent described herein.

The term "PD-1 inhibitor" refers to a moiety (e.g. compound, nucleic acid, polypeptide, antibody) that decreases, inhibits, blocks, abrogates or interferes with the activity or expression of PD-1, including variants, isoforms, species homologs of human D-1 (e.g., mouse) and analogs that have at least one common epitope with PD-1. A PD-1 inhibitor as used herein refers to any moiety that antagonizes PD-1 activity or expression. PD-1 inhibitor efficacy can be measured, for example, by its inhibitor concentration at 50% (half-maximal inhibitor concentration or $IC_{50}$).

The terms "polypeptide" and "protein" are used interchangeably herein and refer to any molecule that includes at least 2 or more amino acids.

The term "regimen" refers to a protocol for dosing and timing the administration of one or more therapies (e.g., combinations described herein or another active agent such as for example an anti-cancer agent described herein) for treating a disease, disorder, or condition described herein. A regimen can include periods of active administration and periods of rest as known in the art.

Antibodies described herein can be polyclonal or monoclonal and include xenogeneic, allogeneic, or syngeneic forms and modified versions thereof (e.g., humanized or chimeric). An "antibody" is intended to mean a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (Borrebaeck (ed.) (1995) *Antibody Engineering, Second Edition*, Oxford University Press.; Kuby (1997) *Immunology, Third Edition*, W.H. Freeman and Company, New York). Specific molecular antigens that can be bound by an antibody described herein include PD-1 and its epitopes.

The term "monoclonal antibody(ies)" refers to a population of antibody molecules that contain one species of an antigen binding site capable of immunoreacting with a particular epitope of an antigen, whereas the term "polyclonal antibody(ies)" refers to a population of antibody molecules that contain multiple species of antigen binding sites capable of interacting with a particular antigen. A monoclonal antibody, typically displays a single binding affinity for a particular antigen with which it immuno-reacts. For example, the monoclonal antibodies to be used in accordance with the present invention can be made by a variety of techniques, including, for example, the hybridoma method (e.g., Kohler and Milstein., Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Set USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Set USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lon berg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The monoclonal antibodies herein also include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Set USA, pp. 6851-6855 (1984)). "Humanized antibody(ies)" can be considered as a subset of chimeric antibodies described herein.

The term "human" when used in reference to an antibody or a functional fragment thereof (e.g., "humanized antibody(ies))" refers an antibody or functional fragment thereof that has a human variable region or a portion thereof corresponding to human germline immunoglobulin sequences. Such human germline immunoglobulin sequences are described by Kabat et al. (1991) Sequences of Proteins of Immunological Interest, Fifth Edition, U.S. Department of Health and Human Services, NIH Publication No. 91-3242. A human antibody, in the context of the present invention, can include an antibody that binds to PD-1 or variants thereof as described herein. In certain instances, a human antibody is an antibody that possesses an amino acid sequence corresponding to that of an antibody produced by a human and/or has been made using any of the techniques for making human antibodies as disclosed herein. Human antibodies can be produced using various techniques known in the art, including phage-display libraries. Hoogenboom and Winter, Mol. Biol., 227:381 (1991); Marks et al., Mol. Biol., 222:581 (1991). Also available for the preparation of human monoclonal antibodies are methods described in Cole et al., Monoclonal Antibodies and Cancer Therapy, Alan R. Liss, p. 77 (1 985); Boemer et al., Immunol., 147(1):86-95 (1991). See also Van Dijk and Van de Winkel, Curr. Opin. Pharmacol., 0.2.: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE technology). See also, for example, Li et al., Proc. Natl. Acad. Sci. USA, 103:3557-3562 (2006) regarding human antibodies generated via a human B-cell hybridoma technology.

A "humanized antibody" refers to antibodies made by a non-human cell having variable or variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention can include amino acid residues not encoded by human germline immunoglobulin sequences (e.g., mutations introduced by random or site-specific mutagenesis in vitro or by somatic mutation in vivo), for example in the CDRs. Humanized antibodies can also include antibodies in which CDR sequences derived from the germline of another mammalian species, such as a mouse, have been grafted onto human framework sequences.

Humanized forms of non-human (e.g., murine) antibodies are antibodies that contain minimal sequence derived from non-human immunoglobulin. In some embodiments, a humanized antibody is a human immunoglobulin (recipient antibody) in which residues from a hypervariable of the recipient are replaced by residues from an hypervariable region of a nonhuman species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies can comprise residues that are not found in the recipient antibody or in the donor antibody. These modifications can be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions can include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally can also include at least a portion of an immunoglobulin constant region (Fc), which can be a human immunoglobulin. Exemplary methods and humanized antibodies include those described by Jones et al. Nature 321:522-525 (1986); Riechmann et al. Nature 332:323-329 (1988); and Presta, Curr. Op. Struct. Biol. 2:593-596 (1992); Vaswani and Hamilton, Ann. Allergy. Asthma & Immunol. 1: 105-115 (1998); Harris, Biochem. Soc. Transactions 23: 1035-1038 (1995); Burle and Gross, Curr. Op. Biotech. 5:428-433 (1994); and U.S. Pat. Nos. 6,982,321 and 7,087,409.

The term "functional fragment" when used in reference to an antibody refers to a portion of the antibody including heavy or light chain polypeptides that retains some or all of the binding activity as the antibody from which the fragment was derived. Such functional fragments can include, for example, an Fd, Fv, Fab, F(ab'), F(ab)2, F(ab')2, single chain Fv (ScFv), diabody, triabody, tetrabody and minibody. Other functional fragments can include, for example, heavy or light chain polypeptides, variable region polypeptides or CDR polypeptides or portions thereof so long as such functional fragments retain binding activity. Such antibody binding fragments can be found described in, for example, Harlow and Lane, Antibodies: A Laboratory Manual, Cold Spring Harbor Laboratory, New York (1989); Myers (ed.), Molec. Biology and Biotechnology: A Comprehensive Desk Reference, New York: VCH Publisher, Inc.; Huston et al., Cell Biophysics, 22: 189-224 (1993); Pluckthun and Skerra, Meth. EnzymoL, 178:497-515 (1989) and in Day, E. D., Advanced Immunochemistry, Second Ed., Wiley-Liss, Inc., New York, NY (1990). Antibody Engineering, Second Edition, Oxford University Press, 1995.

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha ($\alpha$), delta ($\delta$), epsilon ($\epsilon$), gamma ($\gamma$) and mu ($\mu$), based on the aminoacid sequence of the heavy chain constant region. The distinct heavy chains differ in size: $\alpha$, $\delta$ and $\gamma$ contain approximately 450 amino acids, while and F contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa ($\kappa$) of lambda ($\lambda$) based on the amino acid sequence of the constant domains. Light chain amino acid sequences are well known in the art. A light chain can be a human light chain.

The term "variable domain" or "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains can differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) 5th ed. A variable region can be a human variable region.

A CDR refers to one of three hypervariable regions (HI, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., Biol. Chem. 252:6609-6616 (1977); Kabat, Adv. Prot. Chem. 32: 1-75 (1978)). CDR region sequences also have been defined structurally by Chothia as those residues that are not part of the conserved β-sheet framework, and thus are able to adapt different conformations (Chothia and Lesk, Mol. Biol. 196:901-917 (1987)). Both terminologies are well recognized in the art. The positions of CDRs within a canonical antibody variable domain have been determined by comparison of numerous structures (Al-Lazikani et al., Mol. Biol. 273:927-948 (1997); Morea et al., Methods 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly skilled in the art.

EXAMPLES

It will be appreciated that the following examples are intended to illustrate but not to limit the present disclosure. Various other examples and modifications of the foregoing description and examples will be apparent to a person skilled in the art after reading the disclosure without departing from the spirit and scope of the disclosure, and it is intended that all such examples or modifications be included within the scope of the appended claims. All publications and patents referenced herein are hereby incorporated by reference in their entirety Example 1: Synthesis of Compound of Formula (Ia)

The compounds of Formula (I), (Ia), and (II), can be synthesized by the methods provided in PCT/CN2020/07791, which is herein incorporated by reference in its entirety. In some embodiments, the syntheses of compounds described herein are accomplished using means described in the chemical literature, using the methods described herein, or by a combination thereof.

Example 2: Tumor Volume

Reagents: GH21001 (TNO-155), GH21005 (compound of Formula Ia) were supplied by HUYA Biosciences, USA, RMC-4550 was purchased from MCE, China. Osimertinib was purchased from Selleck, China. Cisplatin was purchased from Qilu Pharma, China. Anti-PD-1 (RMP1-14) and Rat IgG2a antibodies were purchased from BioXCell (China).

Procedures involving the care and use of animals in this study were reviewed and approved by the Institutional Animal Care and Use Committee (IACUC) of Crown Biosciences prior to execution. During the study, the care and use of animals were conducted in accordance with the regulations of the Association for Assessment and Accreditation of Laboratory Animal Care (AAALAC). Animals (6-8 weeks) were obtained from Shanghai Lingchang Biotechnology Co., Ltd (Shanghai, China) and were allowed to acclimate prior to tumor cell inoculation.

All cell lines were maintained in culture and cells in exponential growth phase were harvested and quantitated by cell counter before tumor inoculation. MC38 tumor cells ($1\times10^6$) in 0.1 ml of PBS were inoculated into the right front flank of female C57/Bl animals, mean tumor size approximately 112 mm$^3$ at the start of treatment.

Figure 1B:
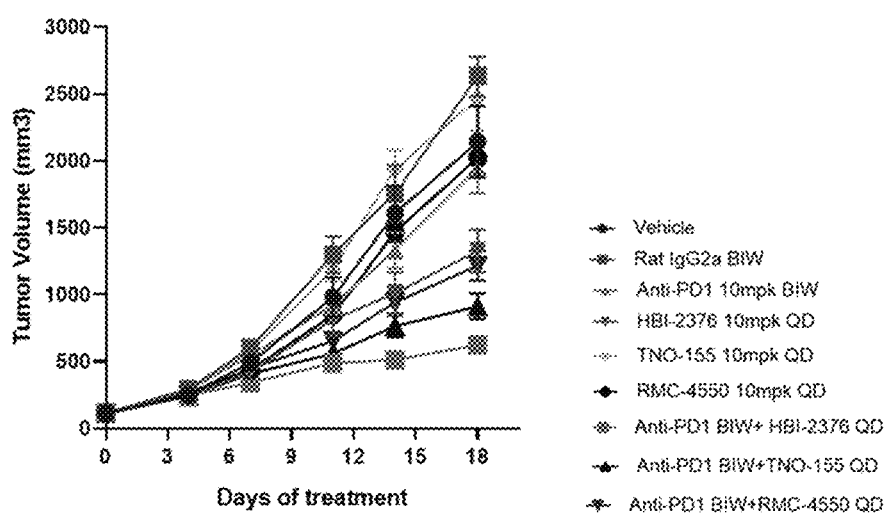

The date of randomization and treatment initiation was denoted as day 0. Tumor volumes were measured twice per week in two dimensions using a caliper, and the volume will be expressed in mm3 using the formula: $V=(L\times W\times W)/2$, where V is tumor volume, L is tumor length (the longest tumor dimension) and W is tumor width (the longest tumor dimension perpendicular to L). Dosing volume was 10 mL/kg/day. GH21001 and GH21005 were dissolved in HP-β-CD was dissolved with 200 ml of 50 mM sodium citrate (pH=4.2). Anti-PD-1 and Rat IgG2a were diluted in PBS. RMC-4550 was diluted in 1% Capitsol in 50 mM sodium citrate (pH=5.0) 0.5% dosing solution of Osmertinib was diluted in 2% DMSO/30% PEG300. The results of this study are depicted in FIGS. 1A and 1B.

Example 3: FACS and Cytokine Analysis

Upon termination, tumors were collected. A portion of the tumor was minced and snap frozen immediately for protein isolation or tumor tissue was dissociated for FACs analysis. Another portion of the tumor was fixed in 10% neutral buffered formalin prior to processing into paraffin blocks.

Tumor dissociation: Upon termination animals bearing MC38 tumors, tumors and blood was harvested 12 hours post last dose. Tumors were enzymatically and mechanically dissociated using The Tumor Dissociation Kit (130-096-730) Miltenyi Biotec MACS Technology. Mononuclear blood cells (PBMCs) were isolated from whole blood using Histopaque-1077 (Sigma).

Cytokine detection assay: V-Plex Proinflammatory Panel 1 Mouse Kit (Mesoscale Discovery) was used to determine cytokine levels in plasma isolated from tumor bearing animals 2 hours post last dose. Plasma from tumor bearing animals was analyzed as described by the manufacture's guidelines. Briefly, diluted plasma is introduced to the MSD plate pre-coated with capture antibodies to the following cytokines, IFN-7, IL-10, IL-2, IL-4, IL-5, IL-6, KC/GRO, IL-10, IL-12p70, and TNF-α. After incubation, samples are washed and incubated with secondary detection antibody, (MSD SULFO-TAG™). Electrochemiluminescence detection from the assay is analyzed on the Meso Scale Discovery platform and cytokine levels calculated according to manufacturer's control samples. The results of this study are depicted in FIGS. 2A, 2B and 2C.

As can be seen in FIGS. 2A and 2B, anti-PD1 monotherapy in the MC38 tumor results in increases in both KC/GRO and TNF-alpha. While treatment of with the compound of Formula (Ia) led slight decreases in KC/GRO and TNF-alpha. However, the combination treatment of both anti-PD-1 and the compound of Formula (Ia) led to significant increases in both KC/GRO and TNF-alpha, evidencing a synergistic effect between the anti-PD-1 and the compound of Formula (Ia). This synergistic effect corroborated the results of the tumor volume assay as depicted in FIG. 1B. FIGS. 2A and 2B also showed the same synergistic relationship between RMC-4550 and anti-PD-1, and the same with GH21001 (TNO-155) and anti-PD-1, evidencing that compounds of Formula (I) and Formula (II) exhibit a synergistic effect with anti-PD-1 when administered to tumors.

Example 4: M1/M2 Macrophage Expression

Whole tumors (MC38 tumors from Examples 2-3) treated with the treatment groups utilized in Examples 2-3 were further tested for M1/M2 macrophage and CD8 expression. See FIGS. 3A, 3B and 3C.

Figure 3A:
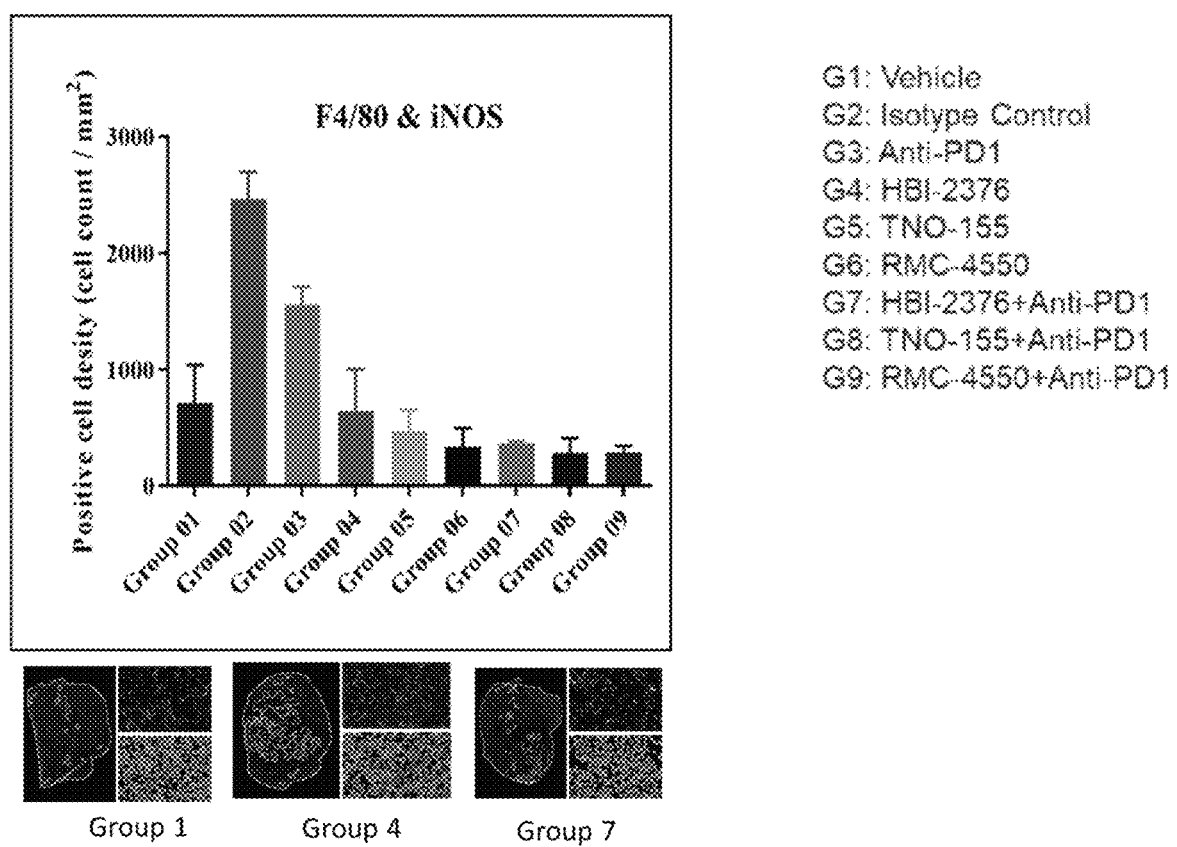
FIGS. 3A, 3B and 3C show M1 (FIG. 3A), M2 (FIG. 3B) and CD8 (FIG. 3C) expression levels in MC38 tumors.
Figure 3B:
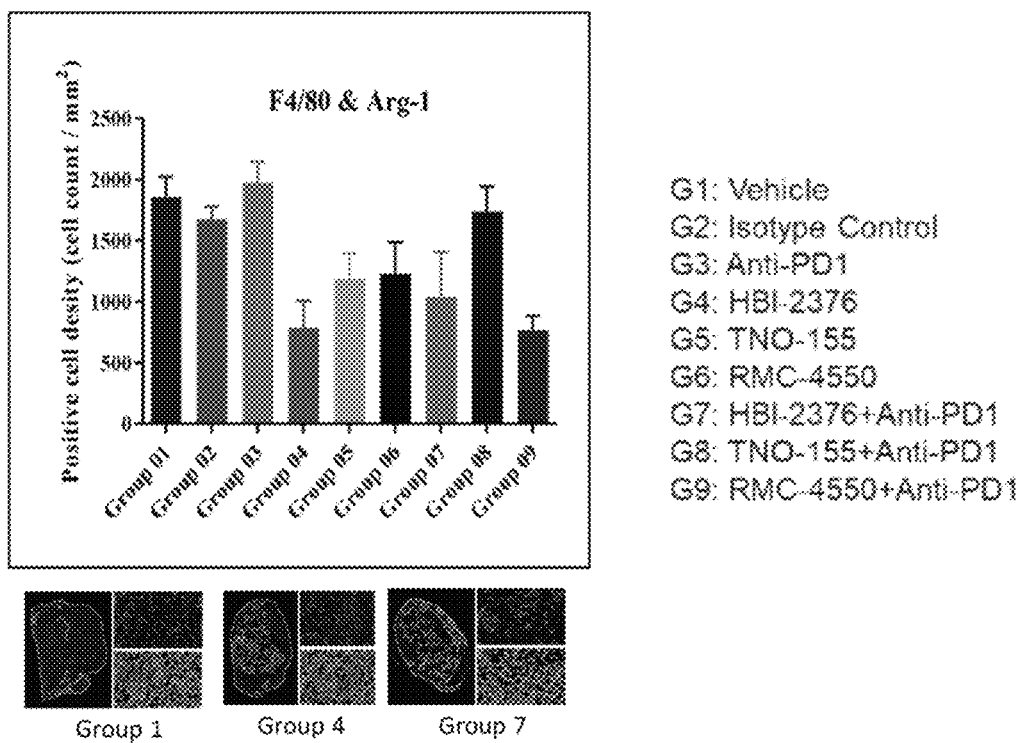
Figure 3C:
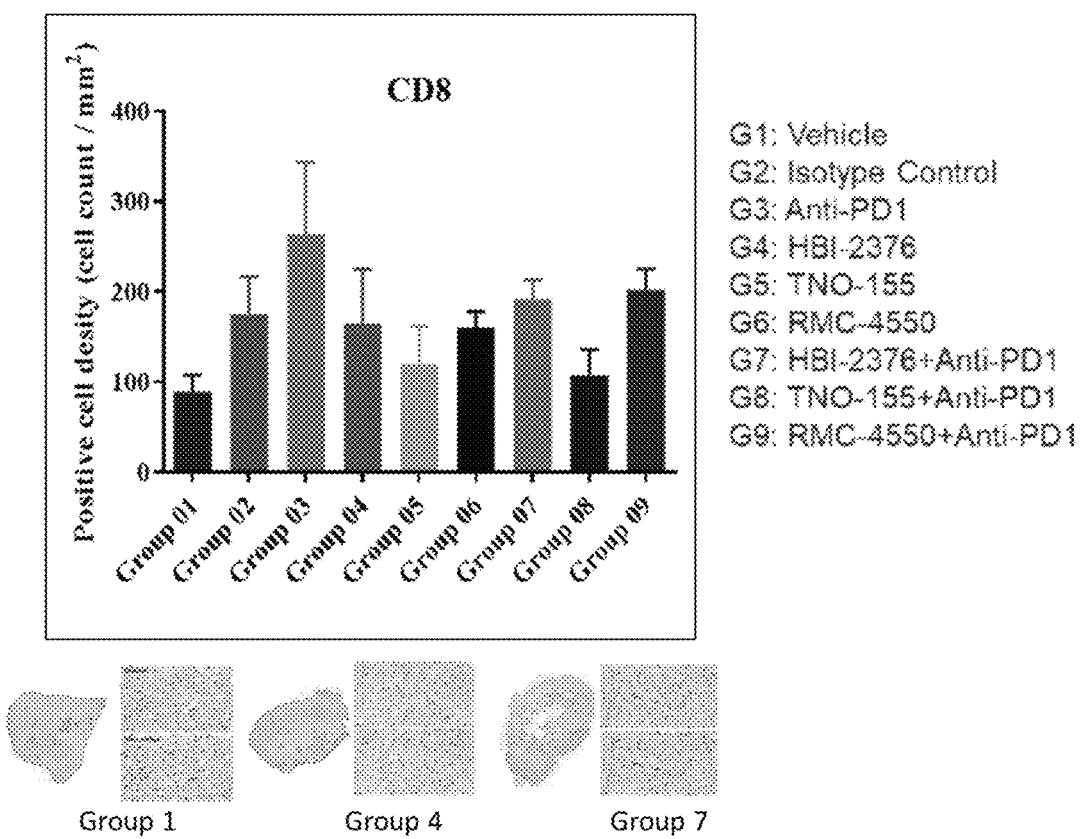

Taken as whole, FIGS. 3A and 3B show that the combination treatment of anti-PD-1 and the compound of Formula (Ia) results in the greatest M1/M2 ratio of all treatment groups. These findings are further supported in IHC assays (FIGS. 3A and 3B; lower panels).

Immunohistochemistry: Freshly collected tumor tissues were placed in 10% NBF and fixed for 24 hours at RT. Tumor tissue was trimmed and rinsed in running water. The specimens were transferred to the Vacuum Tissue Processor (VP1-JC, SAKURA) for dehydration, then embedded into FFPE blocks using Tissue embedding center (TEC 5-EM JC-2, SAKURA). FFPE blocks were sectioned with a manual rotary microtome (HistoCore MULTICUT, Leica), 4 μm thickness/section. Reagents for IHC and antigen retrieval including Bond™ Epitope Retrieval Solution 1 (Bond ER1), Bond™ Epitope Retrieval Solution 2 (Bond ER2), Bond™ Dewax Solution, Bond™ Wash were purchased from Leica. Primary antibodies F4/80 [SP115] Abcam ab111101 was used at 1:1000. iNOS(D6B6S) CST 13120 and Arginase-1 (D4E3M) CST 93668S were both used at 1:500 dilution. Anti-rabbit Poly-HRP-IgG (<25 μg/mL) containing 10% (v/v) animal serum in tris-buffered saline/0.09% ProClin™ 950 (ready-to-use) Leica DS9800 was used for secondary detection. For IF signals, TSA 520 and TSA 670 were purchased from YX Biology (China).

All stained sections were scanned with Pannoramic Digital Slide Scanners (3DHISTECH, Pannoramic SCAN). High resolution pictures for whole section were generated and further analyzed. All the images were analyzed with HALO™ platform. IHC Scoring Method: M1=(iNOS and F4/80) macrophage density=double positive cell counts/whole tumor area×100%. M2=(Arg-1/F4/80) macrophage density=double positive cell counts/whole tumor area× 100%. The results of this study are depicted in FIGS. 3A and 3B (lower panel). These results further evidence the improved efficacy of the combination of anti-PD-1 and the compound of Formula (Ia) in treating cancer.

Example 5: Tumor and Blood Immunotyping

Figure 4A:
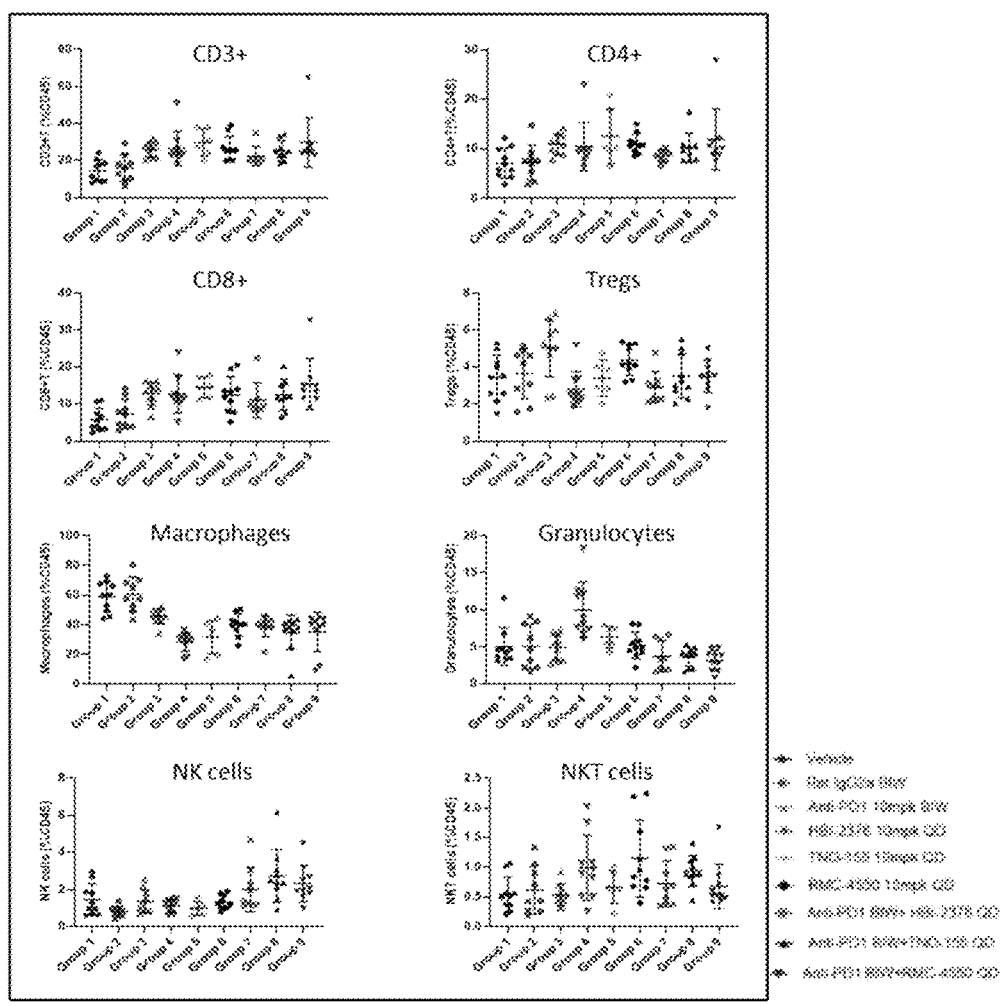
FIGS. 4A and 4B display results for tumor immune profiling and blood immune profiling respectively.
Figure 4B:
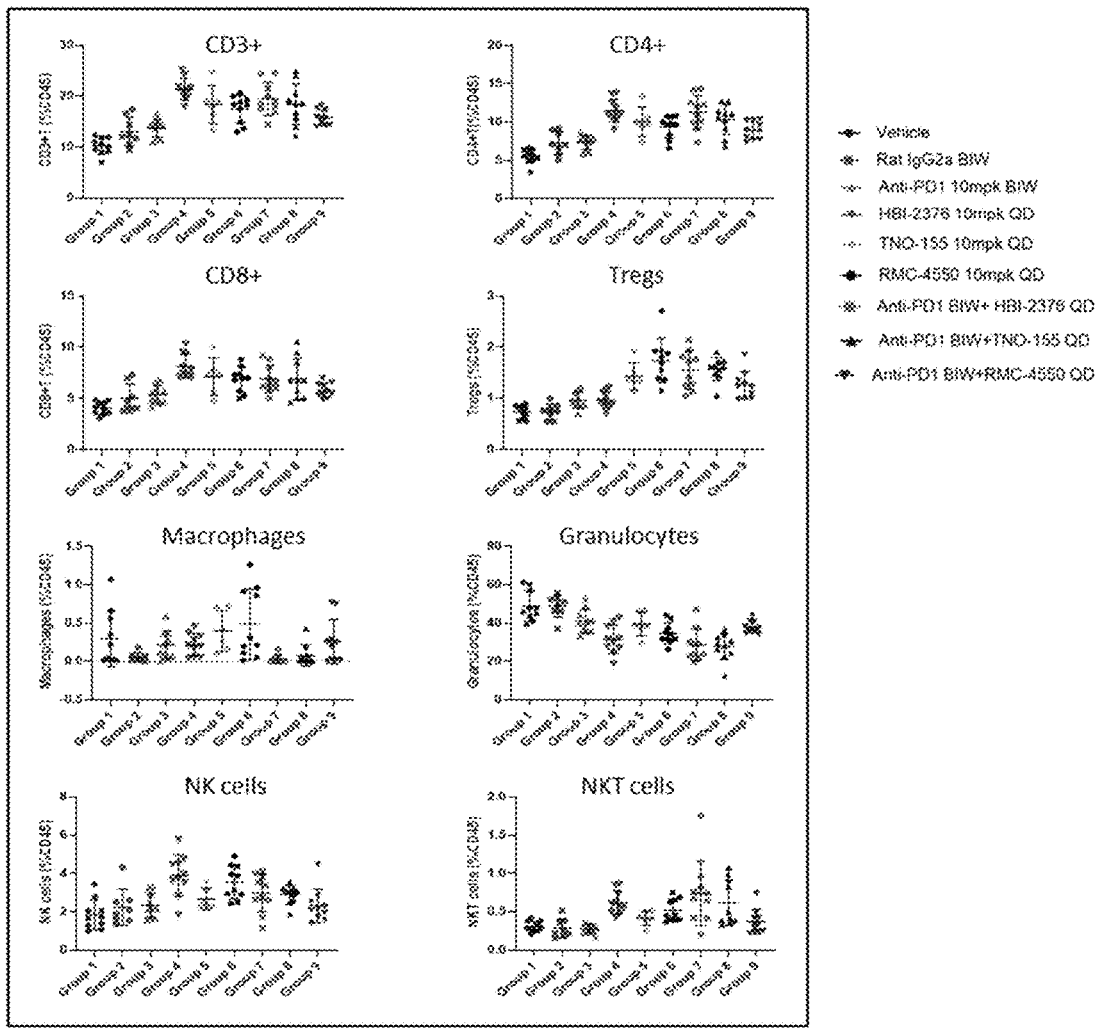

Tumor dissociation: Upon termination animals bearing MC38 tumors, tumors and blood was harvested 12 hours post last dose. Tumors were enzymatically and mechanically dissociated using The Tumor Dissociation Kit (130-096-730) Miltenyi Biotec MACS Technology. Mononuclear blood cells (PBMCs) were isolated from whole blood using Histopaque-1077 (Sigma). Tumor cell suspension, whole lysed blood or isolated PBMCs were resuspended and blocked in staining buffer with 1 μg/ml Fc-Block (Mouse BD Fc Block™ CAT #553141). All antibodies were diluted in Fc Blocking buffer except FoxP3 which was diluted in Permeabilization Buffer. Antibodies were diluted according to Crown Bioscineces optimization. Cell surface markers CD45, CD4, CD335, CD11b, Gr-1, F4/80 were purchased from Biolegend. CD3 was purchased from BD Biosciences. CD8, FoxP3 and L/D BD were purchased from eBiosciences. Data was collected on a BD FACS cytometer and data was analyzed using Kaluza Anaysis Software. See FIGS. 4A and 4B.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating cancer in a patient in need thereof, said method comprising administering to the patient a combination comprising a therapeutically effective amount of a compound having the structure of Formula Ia, or a pharmaceutically acceptable salt or solvate thereof:

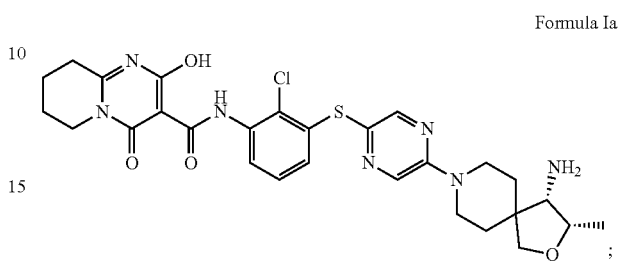

Formula Ia and a PD-1 inhibitor.

2. The method of claim 1, wherein said compound of Formula Ia, or a pharmaceutically acceptable salt or solvate thereof, is administered to said patient in need from about 5 mg/kg to about 25 mg/kg.

3. The method of claim 1, wherein said compound of Formula Ia, or a pharmaceutically acceptable salt or solvate thereof is administered to said patient in need at about 5 mg/kg, about 10 mg/kg, about 15 mg/kg, about 20 mg/kg, or about 25 mg/kg.

4. The method claim 1, wherein said PD-1 inhibitor is a small molecule compound, a nucleic acid, a peptide, a protein, an antibody, a peptibody, a diabody, a minibody, a single-chain variable fragment (ScFv), or a variant thereof.

5. The method of claim 4, wherein said PD-1 inhibitor is a PD-1 inhibitor antibody.

6. The method of claim 5, wherein said PD-1 inhibitor antibody is nivolumab, pembrolizumab, pidilizumab, REGN2810 (SAR-439684), PDR 001, SHR-1210, or MEDI0680.

7. The method of claim 1, wherein said method comprises administering said compound or Formula Ia, or a pharmaceutically acceptable salt or solvate thereof and said PD-1 inhibitor simultaneously or sequentially.

8. The method of claim 1, wherein said cancer is squamous cell carcinoma, nonsquamous cell carcinoma, non-small cell lung cancer (NSCLC), small cell lung cancer, melanoma, hepatocellular carcinoma, renal cell carcinoma, ovarian cancer, head and neck cancer, urothelial cancer, breast cancer, prostate cancer, glioblastoma, colorectal cancer, pancreatic cancer, lymphoma, leiomyosarcoma, liposarcoma, synovial sarcoma, or malignant peripheral sheath tumor (MPNST).

9. The method of claim 1, wherein said patient is treatment naïve.

10. The method of claim 1, wherein said method comprises administering said compound of Formula Ia, or a pharmaceutically acceptable salt of solvate thereof and said PD-1 inhibitor to said patient as a first line therapy.

11. The method of claim 1, wherein said method comprises administering said compound of Formula Ia, or a pharmaceutically acceptable salt or solvate thereof; and said PD-1 inhibitor to said patient following treatment with at least one anti-cancer therapy, wherein said anti-cancer therapy is chemotherapy, radiotherapy, surgery, targeted therapy, immunotherapy, or a combination thereof.

12. The method of claim 1, wherein said method comprises administering said compound of Formula Ia, or a pharmaceutically acceptable salt or solvate thereof; and said PD-1 inhibitor to said patient as a regimen.

13. The method of claim 1, wherein said method comprises administering said compound of Formula Ia, or a pharmaceutically acceptable salt or solvate thereof to said patient orally.

14. The method of claim 1, wherein said method comprises administering said compound of Formula Ia, or a pharmaceutically acceptable salt or solvate thereof to said patient daily; and administering said PD-1 inhibitor to said patient every two weeks.

15. The method of claim 1, wherein said method of treating cancer inhibits metastasis of said cancer in said patient.

16. The method of claim 1, wherein said method of treating cancer prolongs the time to disease progression of said cancer in said patient.

17. The method of claim 1, wherein said method of treating cancer prolongs the survival of said patient.

18. The method of claim 1, wherein said method of treating cancer increases progression-free survival of said patient.

19. The method of claim 1, wherein said method of treating cancer reduces tumor or tumor burden in said patient.

20. A method of treating cancer in a patient in need thereof, said method comprising administering to the patient a combination comprising a therapeutically effective amount of a compound having the structure of Formula Ia, or a pharmaceutically acceptable salt or solvate thereof:

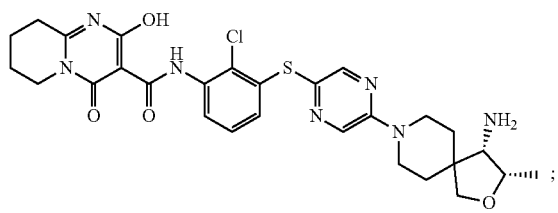

Formula Ia and a PD-1 inhibitor, wherein the amounts of the compound of Formula Ia and PD-1 inhibitor administered to the patient cause an in vivo synergistic effect.

21. The method of claim 20, wherein said compound of Formula Ia, or a pharmaceutically acceptable salt or solvate thereof, is administered to said patient in need from about 5 mg/kg to about 25 mg/kg.

22. The method of claim 20, wherein said compound of Formula Ia, or a pharmaceutically acceptable salt or solvate thereof is administered to said patient in need at about 5 mg/kg, about 10 mg/kg, about 15 mg/kg, about 20 mg/kg, or about 25 mg/kg.

23. The method claim 20, wherein said PD-1 inhibitor is a small molecule compound, a nucleic acid, a peptide, a protein, an antibody, a peptibody, a diabody, a minibody, a single-chain variable fragment (ScFv), or a variant thereof.

24. The method of claim 23, wherein said PD-1 inhibitor is a PD-1 inhibitor antibody.

25. The method of claim 24, wherein said PD-1 inhibitor is nivolumab, pembrolizumab, pidilizumab, REGN2810 (SAR-439684), PDR 001, SHR-1210, or MEDI0680.

26. The method of claim 20, wherein said cancer is squamous cell carcinoma, nonsquamous cell carcinoma, non-small cell lung cancer (NSCLC), small cell lung cancer, melanoma, hepatocellular carcinoma, renal cell carcinoma, ovarian cancer, head and neck cancer, urothelial cancer, breast cancer, prostate cancer, glioblastoma, colorectal cancer, pancreatic cancer, lymphoma, leiomyosarcoma, liposarcoma, synovial sarcoma, or malignant peripheral sheath tumor (MPNST).

27. The method of claim 20, wherein said patient is treatment naïve.

28. The method of claim 20, wherein said method comprises administering said compound of Formula Ia, or a pharmaceutically acceptable salt or solvate thereof, and said PD-1 inhibitor to said patient as a regimen.

29. The method of claim 20, wherein said method comprises administering said compound of Formula Ia, or a pharmaceutically acceptable salt or solvate thereof, to said patient orally.

30. The method of claim 20, wherein said method comprises administering said compound of Formula Ia, or a pharmaceutically acceptable salt or solvate thereof, to said patient daily, and administering said PD-1 inhibitor to said patient every two weeks.

31. The method of claim 20, wherein said method of treating cancer inhibits metastasis of said cancer in said patient, prolongs the time to disease progression of said cancer in said patient, prolongs the survival of said patient, increases progression-free survival of said patient, or reduces tumor or tumor burden in said patient.

* * * * *